(12) United States Patent
Hirata

(10) Patent No.: US 7,749,160 B2
(45) Date of Patent: Jul. 6, 2010

(54) ENDOSCOPE DEVICE

(75) Inventor: Yasuo Hirata, Tokyo (JP)

(73) Assignee: Olympus Corporation (JP)

( * ) Notice: Subject to any disclaimer, the term of this patent is extended or adjusted under 35 U.S.C. 154(b) by 727 days.

(21) Appl. No.: 11/616,221

(22) Filed: Dec. 26, 2006

(65) Prior Publication Data
US 2007/0173695 A1 Jul. 26, 2007

Related U.S. Application Data

(63) Continuation of application No. PCT/JP2005/011634, filed on Jun. 2, 2005.

(30) Foreign Application Priority Data

Jun. 28, 2004 (JP) .......................... P2004-189288

(51) Int. Cl.
*A61B 1/06* (2006.01)
(52) U.S. Cl. .................. 600/179; 600/129; 362/574
(58) Field of Classification Search ................ 600/179, 600/129; 348/68, 75; 362/574
See application file for complete search history.

(56) References Cited

U.S. PATENT DOCUMENTS

| 6,371,907 | B1 | 4/2002 | Hasegawa et al. | 600/146 |
| 7,413,543 | B2 * | 8/2008 | Banik et al. | 600/129 |
| 7,435,218 | B2 * | 10/2008 | Krattiger et al. | 600/175 |
| 2001/0007051 | A1 * | 7/2001 | Nakashima | 600/179 |
| 2002/0188177 | A1 * | 12/2002 | Miyanaga | 600/179 |
| 2003/0018238 | A1 * | 1/2003 | Obata et al. | 600/179 |
| 2004/0215059 | A1 * | 10/2004 | Homan et al. | 600/179 |
| 2004/0215061 | A1 * | 10/2004 | Kimmel et al. | 600/179 |
| 2005/0043586 | A1 * | 2/2005 | Suzushima | 600/160 |
| 2008/0300457 | A1 * | 12/2008 | Hosaka et al. | 600/110 |

FOREIGN PATENT DOCUMENTS

| JP | 60-88921 | 5/1985 |
| JP | 10-328131 | 12/1998 |
| JP | 2001-299677 | 10/2001 |
| JP | 2002-000562 | 1/2002 |
| WO | WO 2005032356 A1 * | 4/2005 |

OTHER PUBLICATIONS

International Search Report PCT/JP2005/011634 dated Aug. 23, 2005 (Japan Patent Office).

* cited by examiner

*Primary Examiner*—John P Leubecker
(74) *Attorney, Agent, or Firm*—Ostrolenk Faber LLP

(57) ABSTRACT

An endoscope device includes an objective lens group that is provided at a distal end of an insertion portion that is inserted into a lumen of a subject and is used to observe or photograph the subject, and an illumination device that is provided at a distal end of the insertion portion and illuminates the subject using LED. The illumination device is provided with LED chips and an LED chip supporting block that supports these LED chips, and at least a portion of the objective lens group is mounted on the LED supporting block.

6 Claims, 22 Drawing Sheets

ENDOSCOPE DEVICE

PRIORITY CLAIM

This application is continuation application of a PCT Application No. PCT/JP2005/011634, filed on Jun. 24, 2005, entitled "endoscope device" whose priority is claimed on Japanese Patent Application No. 2004-189288, filed Jun. 28, 2004. The contents of which are incorporated herein by reference.

BACKGROUND OF THE INVENTION

1. Field of the Invention

The present invention relates to an endoscope device having an objective lens group and an LED-based illumination device provided on an insertion portion that is inserted into the lumen of a subject.

2. Description of Related Art

In endoscope devices that are used in medicine and industry, an objective lens group that is used for observation or for image pickup, and an illumination device that is used to light up the area around a subject inside a lumen are provided at a distal end of an insertion portion that is inserted into the lumen. A device that irradiates light from an externally located light source onto a subject via an optical fiber is widely used for the illumination device, however, in recent years, devices have been developed in which light emitting diodes (referred to below as LED) are directly mounted on the insertion portion, and the area around the subject is lit by light from these LED (for example, refer to Japanese Unexamined Patent Application, First Publication No. 2002-562).

In this conventional endoscope device, an objective lens group and a lens adaptor that incorporates LED are removably fitted onto a distal end of the insertion portion, and the plurality of lenses that make up the objective lens group are mounted on a lens supporting block inside the lens adaptor. LED chips are mounted on a front surface of a metal LED supporting block that is shaped like a circular plate with a hole in it, and this LED supporting block is fixed in position by being fitted onto an outer circumference of a circular cylindrical wall that stands upright on the lens supporting block.

SUMMARY OF THE INVENTION

The endoscope device of the present invention includes: an objective lens group that is provided at a distal end of an insertion portion that is inserted into a lumen of a subject and is used to observe or photograph the subject; and an illumination device that is provided at a distal end of the insertion portion and illuminates the subject using LED. The illumination device is provided with LED chips and an LED chip supporting block that supports these LED chips. At least a portion of the objective lens group is mounted on the LED supporting block.

In the endoscope device of the present invention, it is also possible for objective lenses of the objective lens group, excluding the objective lenses that are mounted on the LED supporting block, to be provided on a separate lens supporting block, and for the LED supporting block to be provided such that it can be mounted on or removed from a front surface of the lens supporting block.

In the endoscope device of the present invention, it is also possible for the LED supporting block to be connected to the lens supporting block via a positioning device.

In the endoscope device of the present invention, it is also possible for an electrical connection portion that is formed by a recess and protrusion engagement for supplying power to the LED chips to be provided between the LED supporting block and the lens supporting block, and the positioning device is formed by the recess and protrusion engagement structure of the electrical connection portion.

In the endoscope device of the present invention, it is also possible for the entire objective lens group to be mounted on the LED supporting block.

In the endoscope device of the present invention, it is also possible for a lens adaptor that is provided with the LED chips and the LED supporting block to be provided at a distal end of the insertion portion main body of the insertion portion, and for the lens adaptor to be provided with: a substantially cylindrical outer cylinder portion that is placed at a front end portion and through which is inserted the LED supporting block; a substantially cylindrical connecting portion that is inserted through the outer cylinder portion and is fixed to a rear end portion of the outer cylinder portion; and a substantially cylindrical connecting ring that is mounted on the connecting portion so as to be freely rotatable, and that connects the LED supporting block to a distal end of the insertion portion main body such that it can be freely attached thereto and removed therefrom, and for a threaded portion that is screwed onto a distal end of the insertion portion main body to be formed on the connecting ring.

In the endoscope device of the present invention, it is also possible for an abutting wall portion that protrudes inwards to be provided at a front end portion of the outer cylindrical portion and, when the LED supporting block is inserted from a rear end portion of the outer cylindrical portion, for a front end portion of the LED supporting block that is positioned at the front in the insertion direction of the LED supporting block to abut against the abutting wall portion.

In the endoscope device of the present invention, it is also possible for the LED supporting block to be formed integrally with the outer cylinder portion.

In the endoscope device of the present invention, it is also possible for a stopper flange that protrudes inwards in a radial direction to be formed at a front end portion of the outer cylinder portion, and for the stopper flange to abut against a placement surface for the LED chips that is located on a front surface of the LED supporting block.

In the endoscope device of the present invention, it is also possible for the placement surface for the LED chips that is located on the front surface of the LED supporting block to be positioned so as to protrude from a front end portion of the outer cylinder portion.

DESCRIPTION OF THE PREFERRED EMBODIMENTS

Next, each of the embodiments of the present invention will be described based on the drawings. Note that in the descriptions of the respective embodiments below, the same descriptive symbols are used for identical components and a repeated description thereof is omitted.

Firstly, the first embodiment shown in FIGS. 1 to 4B will be described.

Figure 2A:
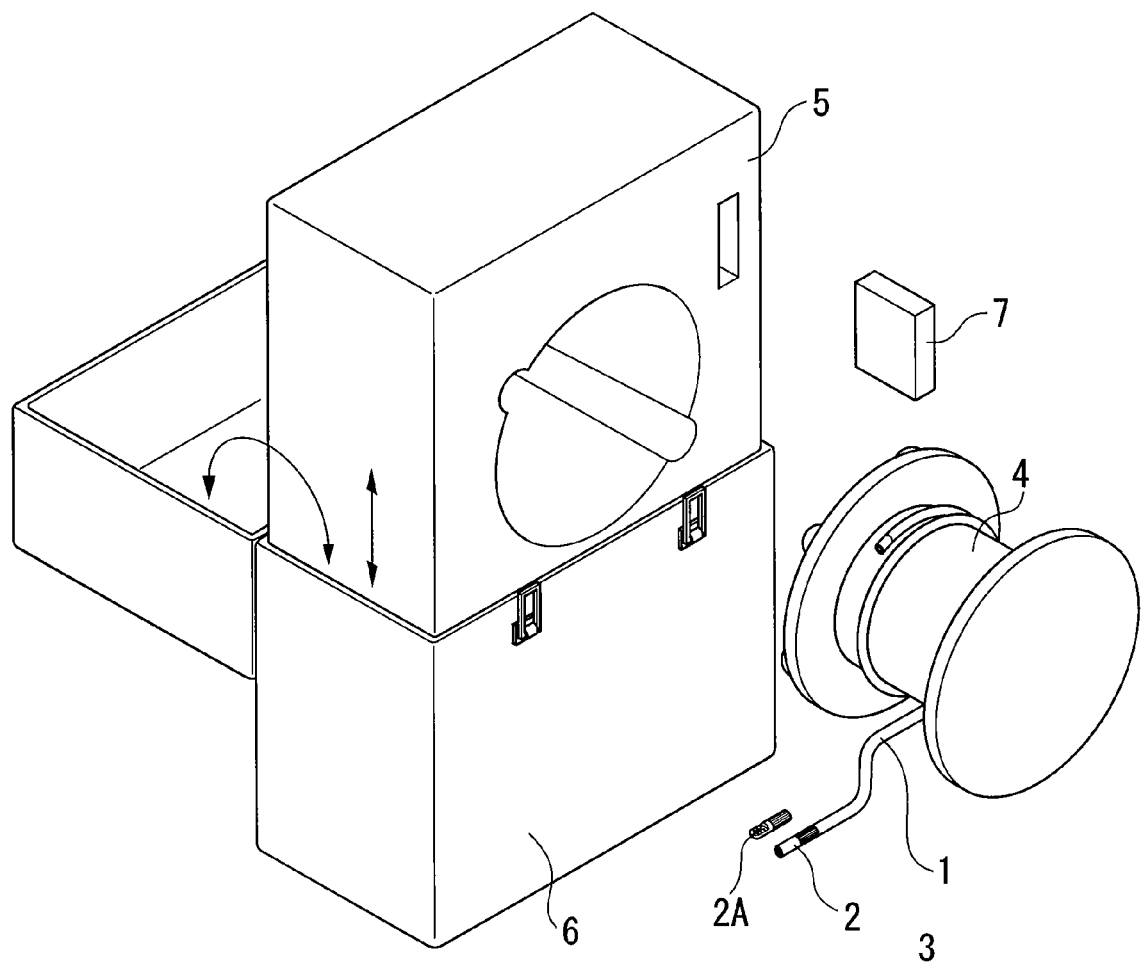
FIG. 2A is a perspective view showing a state in which the endoscope device of the first embodiment has been disassembled.
Figure 2B:
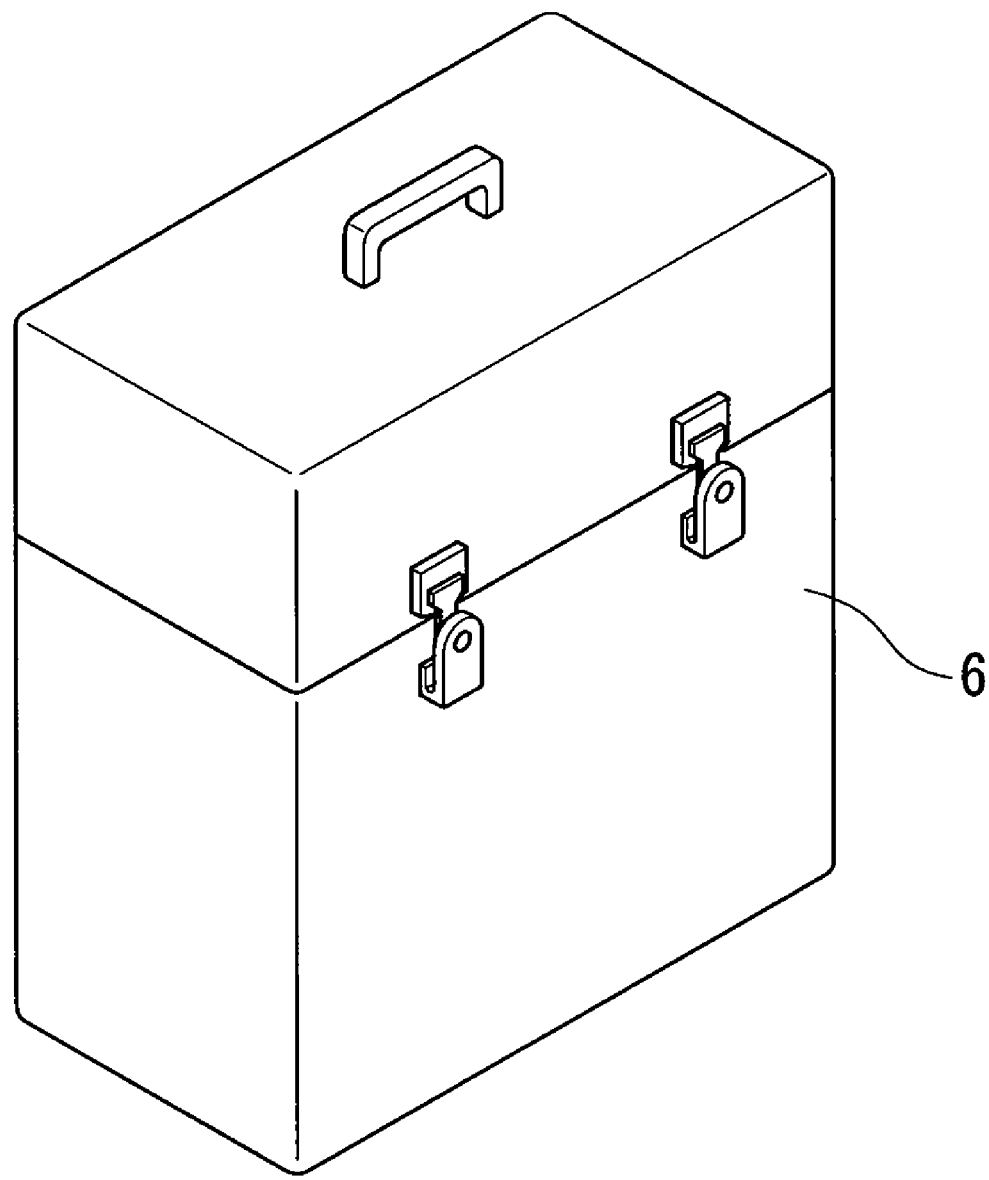
FIG. 2B is a perspective view showing a state in which the endoscope device of the first embodiment has been assembled and housed.

An overall schematic structure of an endoscope device according to the present invention is shown in FIGS. 2A and 2B. As is shown in these drawings, this endoscope device is provided with an insertion portion 3, and a box-shaped device main body 5 that houses the insertion portion 3. A direct-view type of lens adaptor 2 is removably connected to a distal end of a long flexible tube (i.e., an insertion portion main body) 1 of the insertion portion 3. The flexible tube 1 of the insertion portion 3 is wound onto a drum 4 and this drum 4 is rotatably housed in the device main body 5. The device main body 5 housing the drum 4 is stored inside a storage case 6 used for carrying the endoscope device.

This endoscope device has a CCD (not shown) provided as an image pickup device at a distal end of the insertion portion 3, and image signals captured by this CCD pass along a signal wire inside the flexible tube 1 and are output to a signal processing circuit (not shown) that is incorporated in the device main body 5. Signals that have been processed by this signal processing circuit are then projected as video images on an image display unit such as a liquid crystal panel or the like. Note that, in addition to the signal processing circuit, a main power supply circuit (not shown) that is connected to a battery power supply and the like are also incorporated in the device main body 5.

As is described above, the lens adaptor 2 is provided at the distal end of the flexible tube 1 in the insertion portion 3 that is inserted into a lumen. More specifically, a connecting plug 9 that is formed from a hard material such as metal is provided at a distal end of the flexible tube 1, and the lens adaptor 2 is removably provided at a distal end portion of this connecting plug 9. The aforementioned CCD is provided at the distal end portion of the connecting plug 9 as well as electrodes 10a and 10b (see FIG. 1) that supply current to the lens adaptor 2. FIG. 2 shows a replacement lens adaptor 2A and a storage pocket 7 in which the lens adaptor 2A is stored. An insertion portion main body of the insertion portion 3 is formed by portions excluding the lens adaptor 2, namely, by the flexible tube 1 and the connecting plug 9 and the like.

Figure 1:
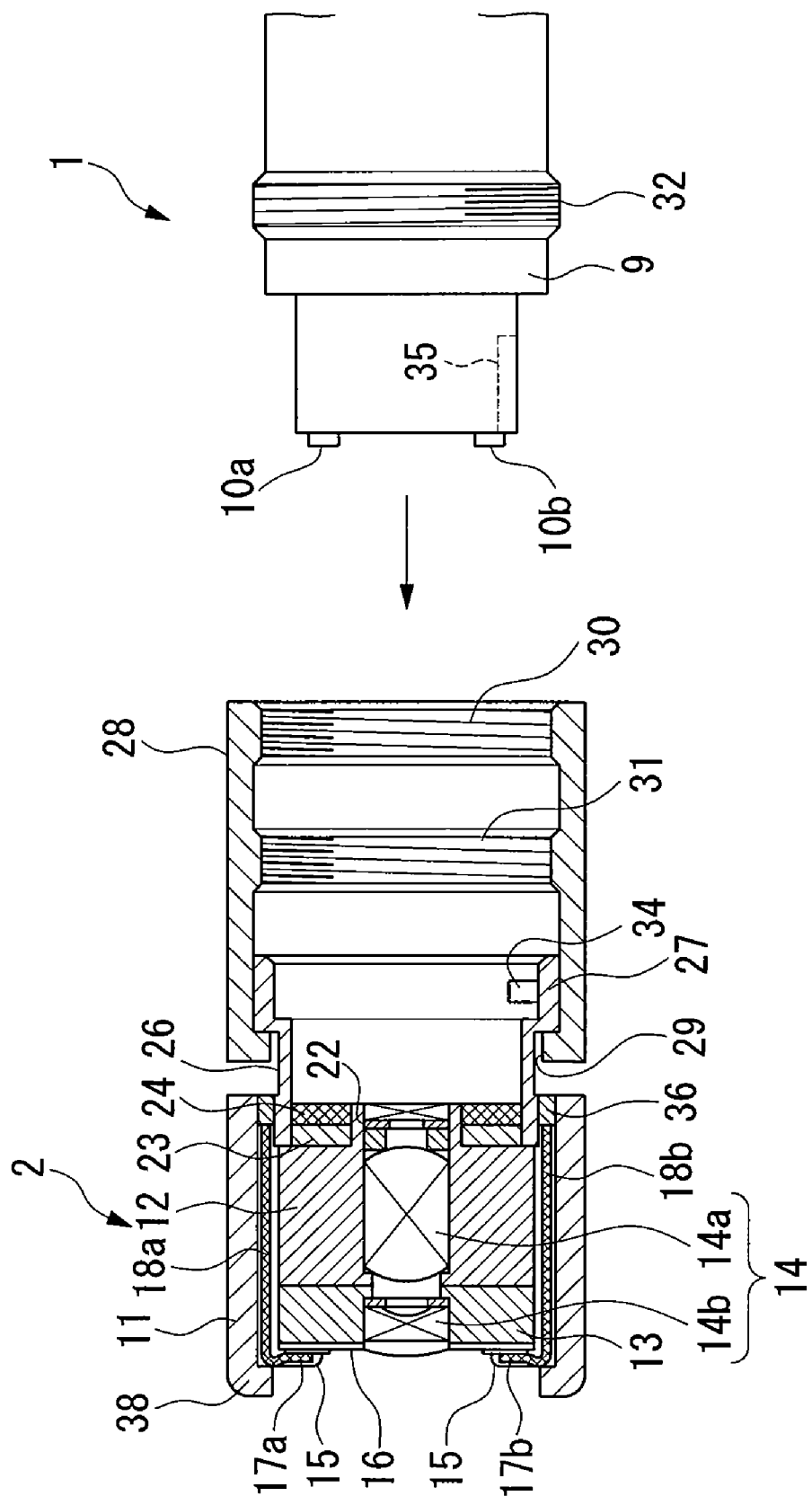
FIG. 1 is a longitudinal cross-sectional view of principal portions illustrating a first embodiment of the present invention.
Figure 3:
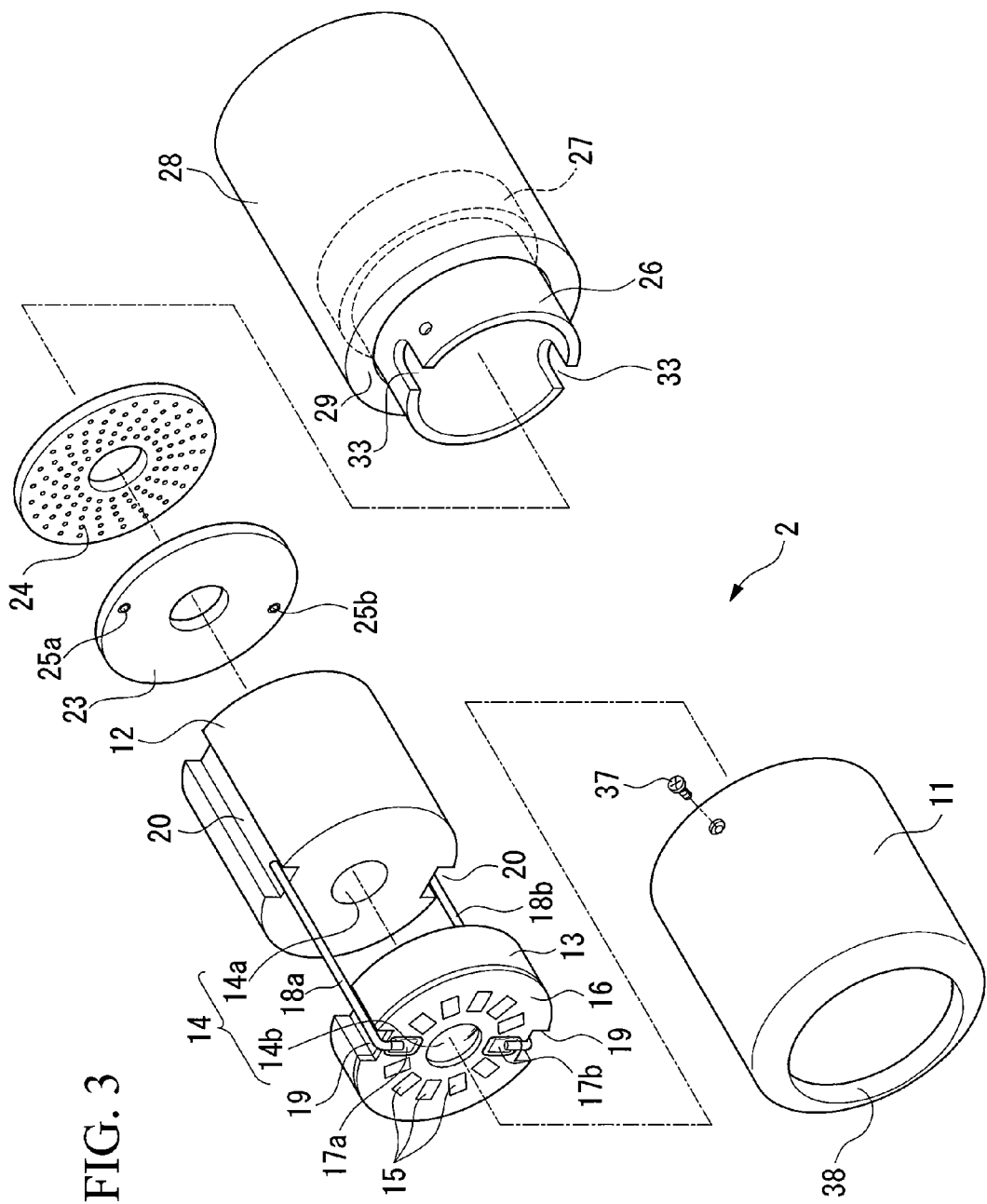
FIG. 3 is an exploded perspective view of principal portions illustrating the first embodiment.

As is shown in FIGS. 1 and 3, in the lens adaptor 2, a lens supporting block 12 and an LED supporting block 13 are housed inside a substantially circular cylinder-shaped adaptor housing (i.e., an outer cylinder portion) 11 so as to be superposed in an axial direction thereof. The overall shape of the lens supporting block 12 is formed substantially as a thick circular cylinder, and principal constituent lenses of an objective lens group 14 (hereinafter, these constituent lenses are called a "first lens group 14a") are housed in an inner circumferential portion thereof. The LED supporting block 13 is formed as a circular plate having a hole therein and having the same outer diameter as the lens supporting block 12. A plurality of LED chips 15 (LED bare chips in this embodiment) are mounted on a front surface of the LED supporting block 13 via a thin non-conductive plate-shaped component 16, and the remaining constituent lenses (hereinafter, these constituent lenses are called a "second lens group 14b") of the objective lens group 14 are housed in an inner circumferential portion of the LED supporting block 13. This LED supporting block 13 is fixed to a front surface of the lens supporting block 12 by an adhesive or the like. Note that the lens supporting block 12 and the LED supporting block 13 are formed from a metal material having excellent thermal conductivity such as aluminum or the like. Moreover, examples of an adhesive agent that may be used as the aforementioned adhesive include silicon having excellent thermal conductivity and a conductive adhesive agent containing metal powder.

The non-conductive plate-shaped component 16 is formed having substantially the same shape as the front surface of the LED supporting block 13, and a pair of electrodes 17a and 17b are embedded in this front surface. In addition, a plurality of LED chips 15 are mounted thereon in a toroidal shape. Front surfaces of the two electrodes 17a and 17b lie exposed from the non-conductive plate-shaped component 16, and are joined by wire bonding to the plurality of LED chips 15 that are mounted on the non-conductive plate-shaped component 16. Wires 18a and 18b are respectively connected to the electrodes 17a and 17b, and each of these wires 18a and 18b extend rearward along guide grooves 19 and 20 that are formed on outer surfaces of the LED supporting block 13 and the lens supporting block 12. Note that, although not shown in the drawings, suitable sealing glass is installed onto the front surface of the LED supporting block 13 including the LED chips 15.

Figure 4A:
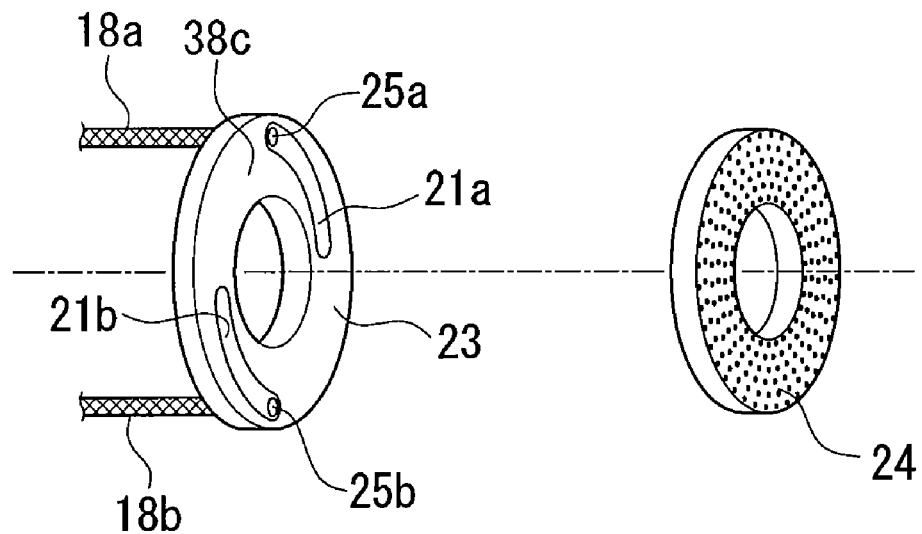
FIG. 4A is a perspective view of principal portions illustrating the first embodiment.
Figure 4B:
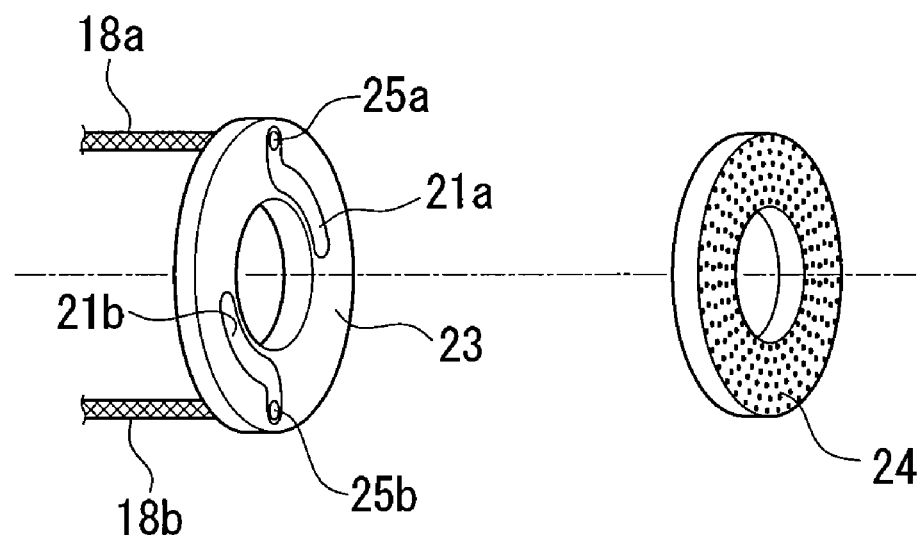
FIG. 4B is a perspective view of principal portions illustrating a variant example of the first embodiment.

As is shown in FIG. 1, a small diameter cylindrical wall 22 stands upright from a rear surface of the lens supporting block 12, and an electrode substrate 23 in the shape of a circular plate having a hole therein as well as conductive rubber 24 are fitted onto an outer circumference of the cylindrical wall 22. As is shown in FIGS. 3 and 4A, a pair of through holes 25a and 25b that penetrate in the plate thickness direction are formed in the electrode substrate 23, while a pair of conductor patterns 21a and 21b that form an electrode are formed on a rear surface of the electrode substrate 23. As is shown in FIG. 4A, the respective conductor patterns 21a and 21b extend so as to curve gently inwards in a radial direction from a portion close to an outer side in the radial direction where the through holes 25a and 25b are formed. End portions of the respective wires 18a and 18b are soldered to the respective conductor patterns 21a and 21b via the corresponding through holes 25a and 25b. Note that, as is shown in FIG. 4B, it is also possible for the conductor patterns 21a and 21b to extend from the through hole 25a and 25b portions directly inwards in the radial direction, and from there to extend in an arc shape that is concentric with the inner circumferential surface of the electrode substrate 23. A rear conductive rubber 24 is pressed against the respective conductor patterns 21a and 21b.

The conductive rubber 24 is formed by embedding conductive components such as nickel particles or gold plated metal particles in a non-conductive rubber material such as silicon rubber in a dotted pattern. Normally, this is known as a dot type of anisotropic conductive rubber or the like. Because the conductive rubber 24 has the above described structure, if the rubber material, which is an elastic object, is pressed in the thickness direction thereof, the conductivity between conductive components whose density has been increased by the resulting compression deformation increases so that conductivity in the thickness direction is allowed. However, because the rubber material is a non-conductive component, a non-conductive state is maintained at this time in directions other than the thickness direction (for example, the circumferential direction) of the rubber material.

As is described below, when the lens adaptor 2 is connected, the conductive rubber 24 is pressed from the rear by the electrodes 10a and 10b of the connecting plug 9. As a result, only those localized portions that are pressed by the respective electrodes 10a and 10b become conductive so that only the electrodes of the electrode substrate 23 and the connecting plug 9 that are located in positions facing each other at this time become electrically connected.

A substantially circular-cylinder shaped guide component (i.e., joining portion) 26 that protrudes rearwards from the adaptor housing 11 is provided protruding at a rear end portion of the lens supporting block 12. An enlarged diameter cylindrical wall 27 whose diameter is enlarged in a step shape is formed integrally with a rear portion of this guide component 26. A circular cylinder-shaped connecting ring 28 is fitted to this enlarged diameter cylindrical wall 27 such that it can be displaced in an axial direction and in a pivot direction. An inward protruding stopper flange 29 against which the step portion of the enlarged diameter cylindrical wall 27 is able to abut is formed integrally with one end portion of the connecting ring 28. Moreover, a first female thread (i.e., threaded portion) 30 and a second female thread (i.e., threaded portion) 31 are provided a predetermined distance apart in the axial direction on an inner circumferential surface of the connecting ring 28.

Note that, as is shown in FIGS. 1 and 3, with the connecting ring 28 placed inside it the guide component 26 is fixed together with a spacer ring 36 by a screw 37 to an inner surface of a rear portion of the adaptor housing 11. At this time, a front end surface of the guide component 26 is pressed against the rear surface of the electrode substrate 23. In addition, an inwardly protruding stopper flange 38 is formed at a front end portion of the adaptor housing 11, and the front end portion of the LED supporting block 13, which is assembled as a single unit together with the lens supporting block 12 and the electrode substrate 23, is prevented from being withdrawn by this stopper flange 38. Accordingly, all three of the LED supporting block 13, the lens supporting block 12, and the electrode substrate 23 are sandwiched between the stopper flange 38 and the guide component 26 and, in this state, are fixed inside the adaptor housing 11. Moreover, as is shown in FIG. 3, recessed grooves 33 are formed in a front end portion of the guide component 26 in order to prevent it making contact with the soldered portions on the conductor patterns 21a and 21b.

In contrast, a male thread 32 used for fixing is formed on an outer circumferential surface of the connecting plug 9. By screwing the first female thread 30 and the second female thread 31 of the connecting ring 28 in sequence onto the male thread 32, the lens adaptor 2 can be connected to the connecting plug 9. Namely, if the connecting ring 28 of the lens adaptor 2 is screwed onto the front end portion of the connecting plug 9 and if, in this state, the connecting ring 28 is rotated in a predetermined direction, then any displacement in the axial direction of the connecting ring 28 is restricted by the stopper flange 29 abutting against the step portion of the enlarged diameter cylindrical wall 27. In this state, the male thread 32 of the connecting plug 9 is fastened in sequence into the first female thread 30 and then the second female thread 31, and the electrodes 10a and 10b that protrude from the front end surface of the connecting plug 9 press against the conductive rubber 24 so as to become electrically connected to the conductor patterns 21a and 21b on the electrode substrate 23 via the conductive rubber 24. Note that, after the male thread 32 of the connecting plug 9 has been screwed into the second female thread 31, the engagement thereof with the first female thread 30 is undone, however, the first female thread 30 functions as a stopper to prevent the connecting plug 9 falling out in the unlikely event that the engagement becomes undone between the male thread 32 and the second female thread 31.

The symbols 34 and 35 in FIG. 1 denote a positioning protrusion and a receiving groove that are formed respectively in the guide cylinder 27 and the connecting plug 9 and that position both 27 and 9 in the rotation direction by engaging with each other.

In the endoscope device of the present embodiment, as in the structure described above, the objective lens group 14 that is located on an axial center portion of the lens adaptor 2 is separated into a first lens group 14a and a second lens group 14b, and the second lens group 14b is directly mounted on the axial center portion of the LED supporting block 13. Accordingly, compared with a structure in which the LED supporting block 13 is screwed onto an outer circumference of a separate component housing the objective lens group 14, it is possible to more easily secure the space needed to position the LED chips 15 on the front surface of the LED supporting block 13. As a result, it is possible to reduce the outer diameter of the LED supporting block 13 and achieve a reduction in the diameter of the lens adaptor 2 (i.e., the distal end of the insertion portion) without altering the diameter of the objective lens which would affect the optical characteristics.

Moreover, in this endoscope device, because the objective lens group is separated and placed on a lens supporting block and an LED supporting block, if necessary, it is possible to separate the lens adaptor 2 and change the combination of the lens supporting block 12 and the LED supporting block 13. Namely, in this embodiment, it is possible to remove the guide component 26 and the spacer ring 36 from the rear portion of the adaptor housing 11 by undoing the screw 37, and, in this state, all three of the LED supporting block 13, the lens supporting block 12, and the electrode substrate 23 can be removed as a single block from the adaptor housing 11. Furthermore, by melting the soldered portions or the like, it is possible to replace the LED supporting block 13 or the lens supporting block 12 for ones having different specifications. If only the LED supporting block 13 is to be replaced, then if a plurality of LED supporting blocks 13 are prepared in advance in which the optical characteristics (i.e., the focal length and angle of view and the like) and light distribution characteristics of the objective lens (i.e., the second lens group 14b) and the LED chips 15 have been combined so as to be optimally matched, it becomes possible to deal flexibly and easily with a variety of observation specifications.

Furthermore, because the connecting ring 28 is mounted on the guide component 26 such that it can rotate freely, when the connecting ring 28 is rotated and the LED supporting block 13 is connected to the distal end of the flexible tube 1, the LED supporting block 13 and the lens supporting block 12 and the like are not rotated with the connecting ring 28. Accordingly, the LED supporting block 13 and the lens supporting block 12 can be easily positioned at the distal end of the flexible tube 1.

Figure 5:
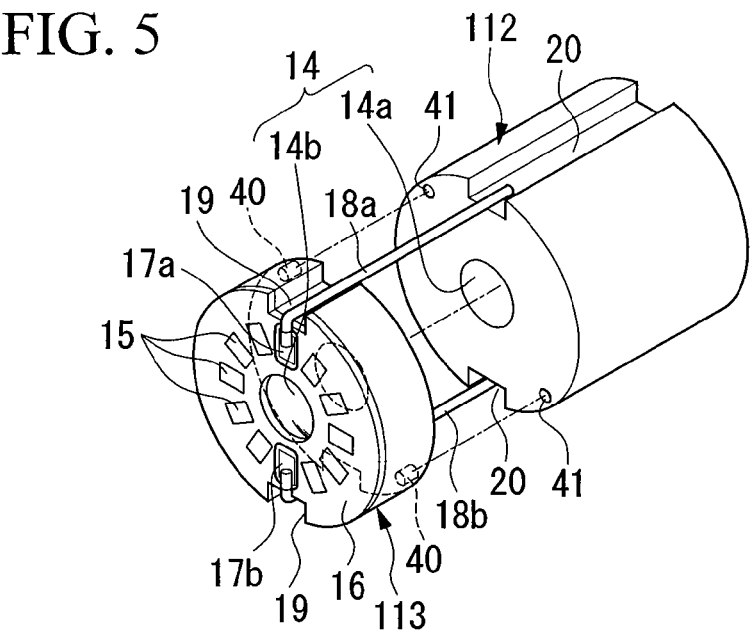
FIG. 5 is an exploded perspective view illustrating a second embodiment of the present invention.

In the endoscope device of this first embodiment no special positioning structure is provided for the LED supporting block 13 and lens supporting block 12 themselves, and when bonding the two together, the axial centers of the two are made to conform to each other using a jig or the like. However, as in a second embodiment shown in FIG. 5, it is also possible to provide positioning projections 40 on one of an LED supporting block 113 and a lens supporting block 112, and to provide engaging holes 41 that engage with the projections 40 on the other of the two supporting blocks 113 and 112. When this type of structure is employed, it is possible to easily and reliably align the axial centers of the two supporting blocks 113 and 112 without having to use a dedicated jig or the like. Note that, in this embodiment, the positioning projection 40 and engaging hole 41 constitute a positioning device.

Figure 6:
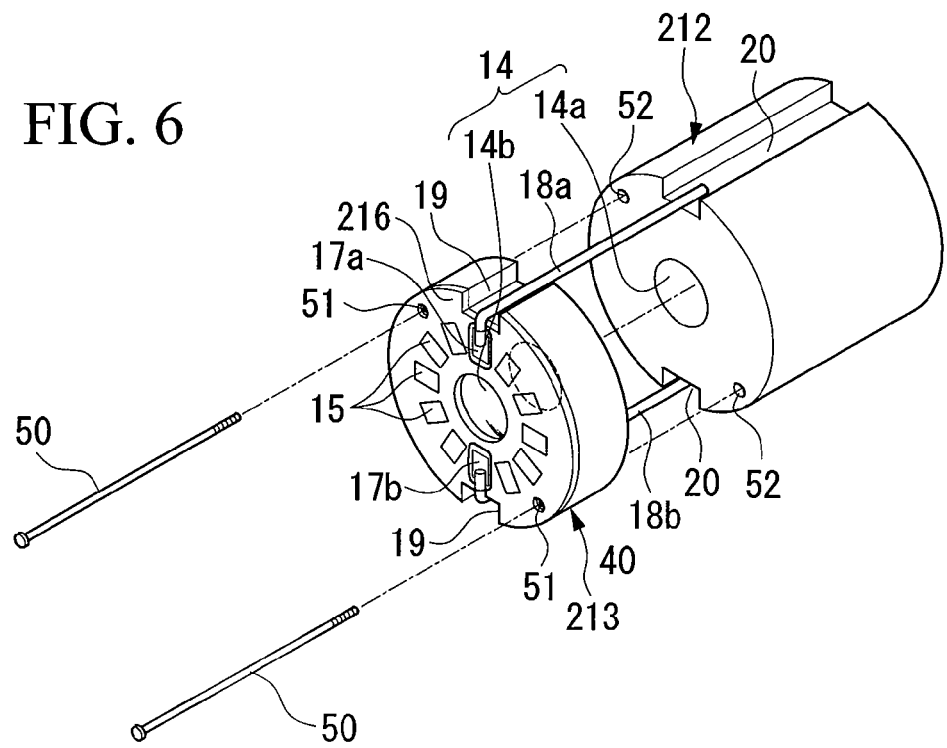
FIG. 6 is an exploded perspective view illustrating a third embodiment of the present invention.

FIG. 6 shows a third embodiment of the present invention. In this embodiment, an LED supporting block 213 and a lens supporting block 212 are joined together using a plurality of axially elongated connecting pins 50. The respective connecting pins 50 are inserted through pin holes 51 that penetrate a non-conductive plate-shaped component 216 and the LED supporting block 213 in the axial direction, and distal end portions thereof that have penetrated the pin holes 51 are screwed into threaded holes 52 in the lens supporting block 212. In the case of this endoscope device, it is possible using the connecting pins 50 to simultaneously align the axial centers of the LED supporting block 213 and the lens supporting block 212 and also fix the two supporting blocks 213 and 212 together. As a result, compared with when the supporting blocks 213 and 212 are adhered together, there is a huge improvement in the workability of the assembly task. Furthermore, when replacing the LED supporting block 213 and lens supporting block 212 with other supporting blocks, this can be achieved simply by unscrewing the connecting pins 50 so that the replacement task also has a high level of workability. Note also that, in this embodiment, the connecting pins 50, the pin holes 51, and the threaded holes 52 constitute a positioning device.

Figure 7:
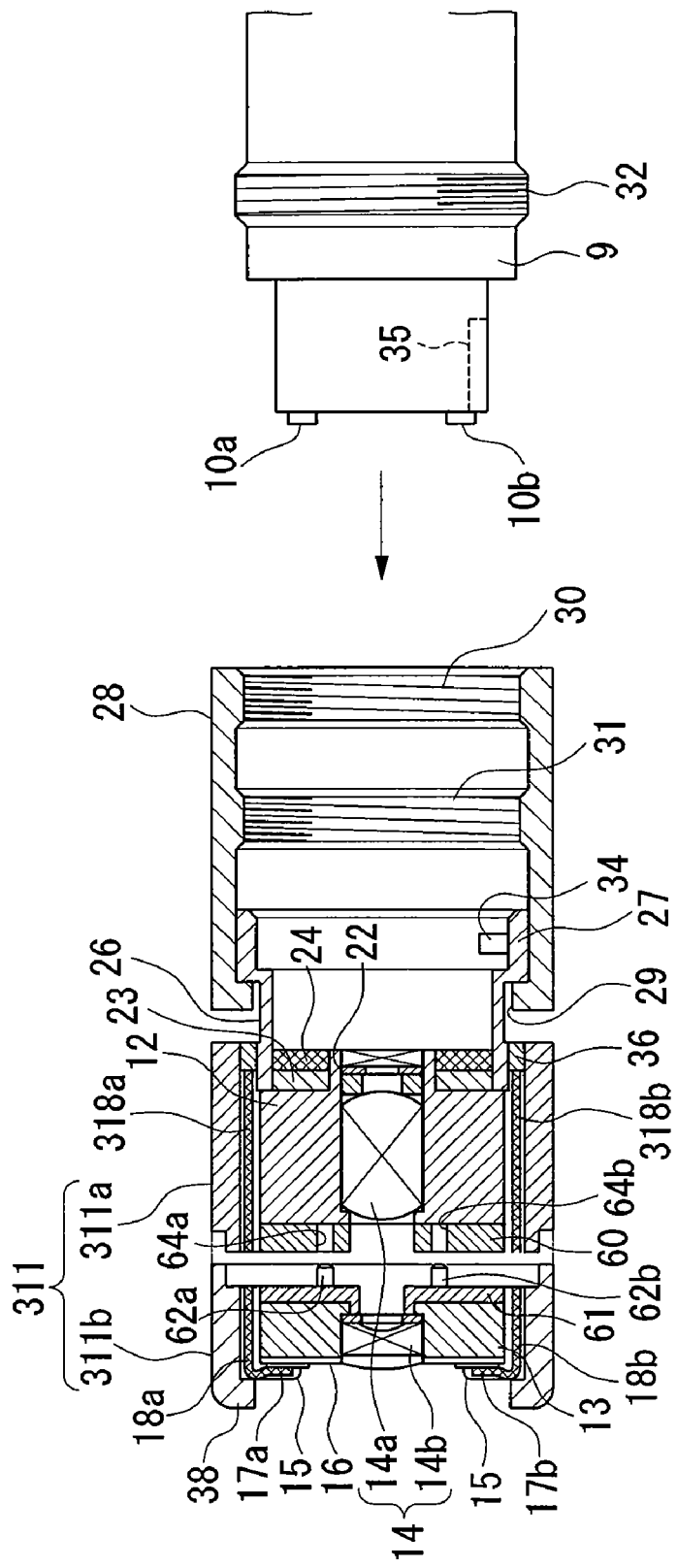
FIG. 7 is a longitudinal cross-sectional view of principal portions illustrating a fourth embodiment of the present invention.
Figure 8:
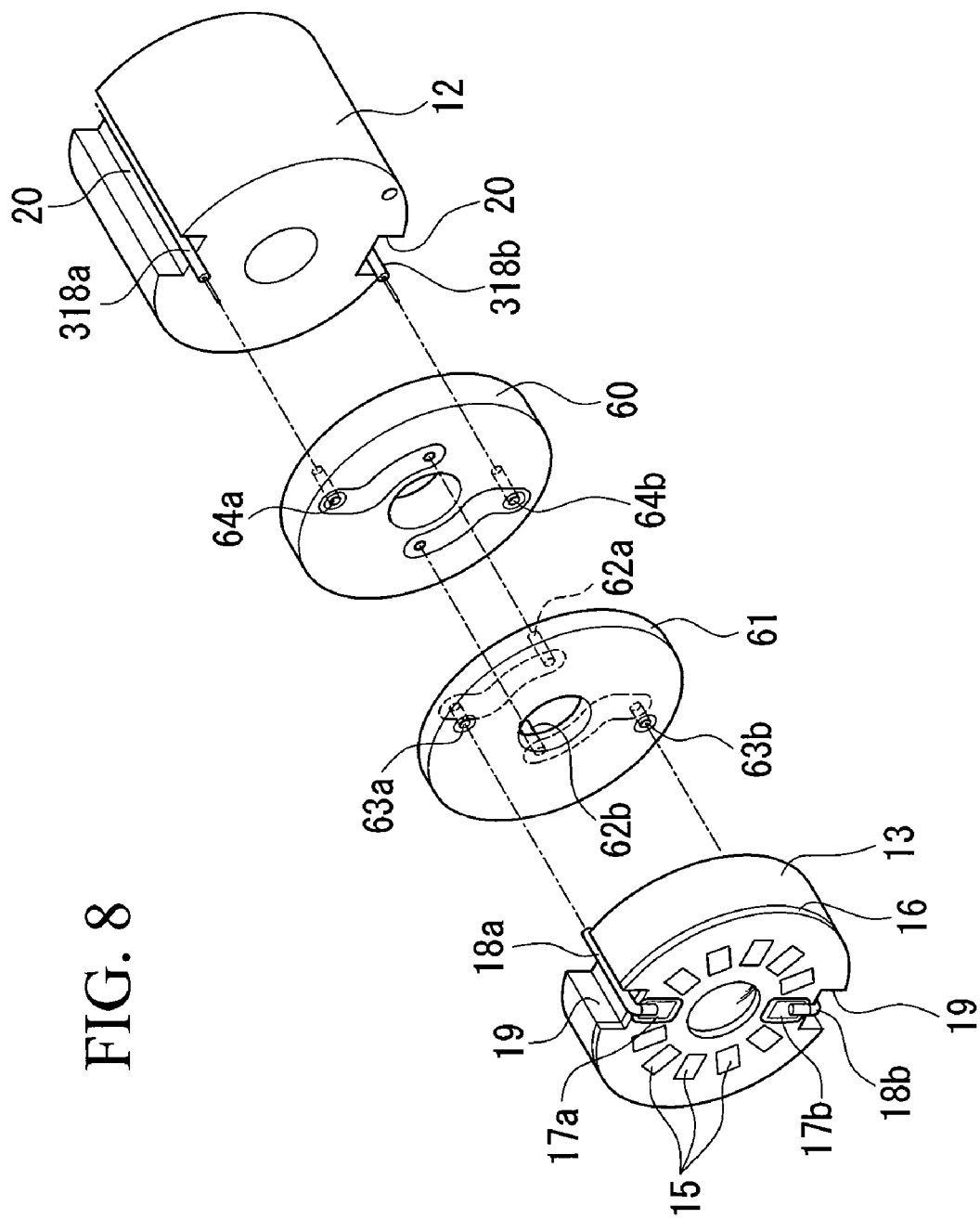
FIG. 8 is an exploded perspective view illustrating a fourth embodiment of the present invention.

Next, a fourth embodiment shown in FIGS. 7 and 8 will be described.

In the endoscope device of this embodiment, the basic structure in which a portion of the objective lenses 14 (i.e., the second lens group 14b) is directly mounted on an inner circumferential portion of the LED supporting block 13 and the remaining objective lenses (i.e., the first lens group 14a) are mounted on the lens supporting block 12 is the same as in the first embodiment, however, a device that enables the LED supporting block 13 to be easily mounted on or removed from the lens supporting block 12 is further employed.

The adaptor housing 311 is separated into a rear portion housing 311a that has the guide component 26 mounted on a rear end portion thereof and houses the lens supporting block 12 and the electrode substrate 23 and the like inside it, and a front portion housing 311b that is located forward of the rear portion housing 311a and houses the LED supporting block 13 and the like inside it. In addition, electrode substrates 60 and 61 are fixed by adhesive respectively to the front surface of the lens supporting block 12 and the rear surface of the LED supporting block 13, and electrode portions of these electrode substrates 60 and 61 are connected together via a recess and protrusion engagement.

Namely, on the electrode substrate 61 on the LED supporting block 13 side, are formed a pair of protruding electrodes 62a and 62a that protrude rearwards and through holes 63a and 63b that penetrate in the thickness direction. Wires 18a and 18b that are drawn forwards from in front of the LED supporting block 13 pass through the through holes 63a and 63b are connected to the protruding electrodes 62a and 62b. The respective protruding electrodes 62a and 62b are formed as circular columns that extend in the axial direction of the electrode substrate 61. In contrast, on the electrode substrate 60 on the lens supporting block 12 side are provided a pair of recessed electrodes 64a and 64b, and wires 318a and 318b that are drawn from the electrode substrate 23 to the rear are connected to these recessed electrodes 64a and 64b. The recessed electrodes 64a and 64b are formed at positions corresponding to the protruding electrodes 62a and 62b, and are able to be engaged with the protruding electrodes 62a and 62b when the axial centers of the lens supporting block 12 and the LED supporting block 13 are aligned. As a result, in this embodiment, the protruding electrodes 62a and 62b are respectively connected to the recessed electrodes 64a and 64b by a recess and protrusion engagement.

In the endoscope device of this embodiment the same basic operation and effects as those of the first embodiment can be obtained, however, because a structure is employed in which the adaptor housing 311 is separated into a front portion housing 311a and a rear portion housing 311b, and the front portion housing 311a can be fitted to and removed from the rear portion housing 311b, the LED supporting block 13 can be easily replaced from the front surface of the adaptor housing 311. In particular, in this embodiment, because power is supplied to the LED chips 15 by the recess and protrusion engagement structure formed by the protruding electrodes 62a and 62b and the recessed electrodes 64a and 64b, it is not necessary for any solder to first be melted before they are removed or fitted. Accordingly, there is a considerable improvement in the workability of the task of replacing the LED supporting block. Moreover, because the recess and protrusion engagement structure formed by the protruding electrodes 62a and 62b and the recessed electrodes 64a and 64b also contributes to the positioning that is performed in order to align the axial centers of the LED supporting block 13 and the lens supporting block 12, it is possible for the apparatus structure to be simplified due to it no longer being necessary to provide a separate positioning portion.

Figure 9:
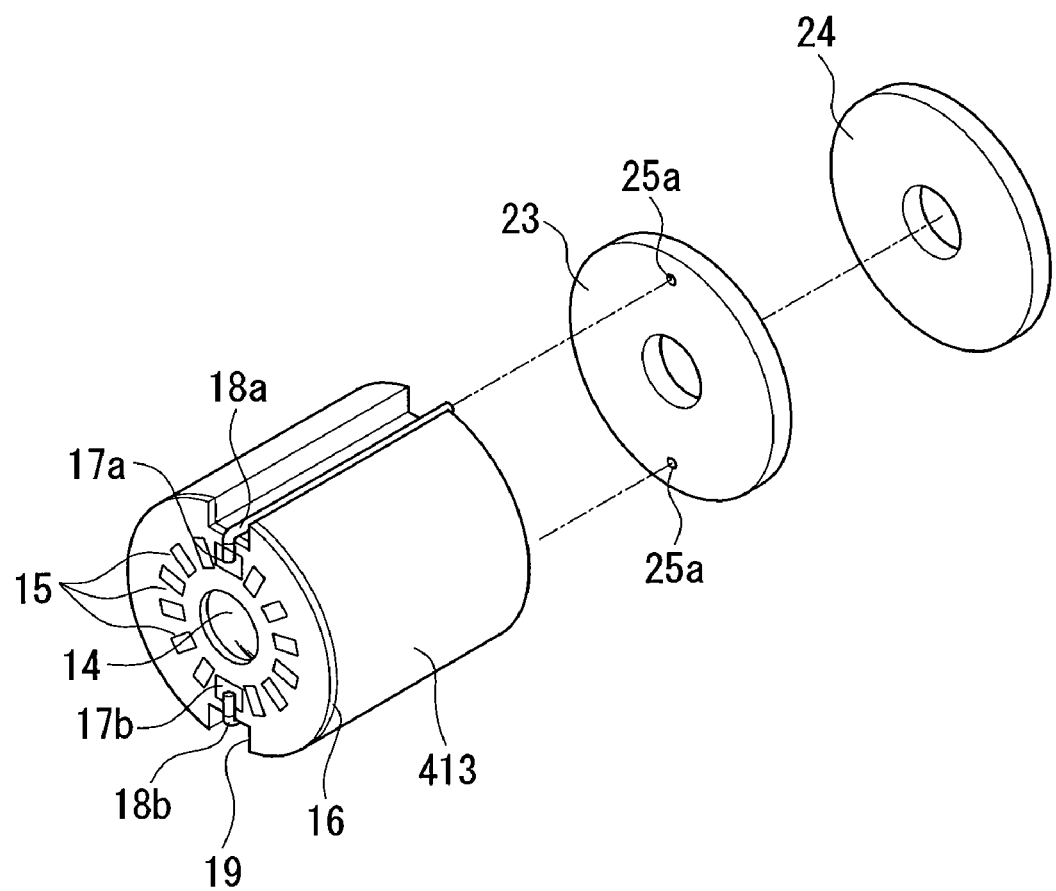
FIG. 9 is an exploded perspective view illustrating a fifth embodiment of the present invention.

Moreover, in all of the embodiments described above, the objective lens group is separated into a first lens group on the lens supporting block side and a second lens group on the LED supporting block side and these lens groups are each mounted on their respective block, however, as in a fifth embodiment shown in FIG. 9, it is also possible to form an LED supporting block 413 as a thick circular cylinder and to mount all of the lens elements of the objective lens group 14 in an inner circumferential portion of the LED supporting block 413. If this type of structure is employed, it is possible to reduce the number of components due to it no longer being necessary to place a separate lens supporting block at a rear portion of the LED supporting block 413, and there is also an improvement in the workability of the assembly task.

Furthermore, as in the aforementioned fifth embodiment, when all of the lens elements (i.e., the first lens group 14a and the second lens group 14b) of the objective lens group 14 are mounted in an inner circumferential portion of the LED supporting block 413, by employing a structure in which the LED supporting block 413 and a guide component are inserted from the same direction into a substantially circular cylinder-shaped adaptor housing, it becomes possible to form the LED supporting block and the guide component as a single unit.

Figure 10:
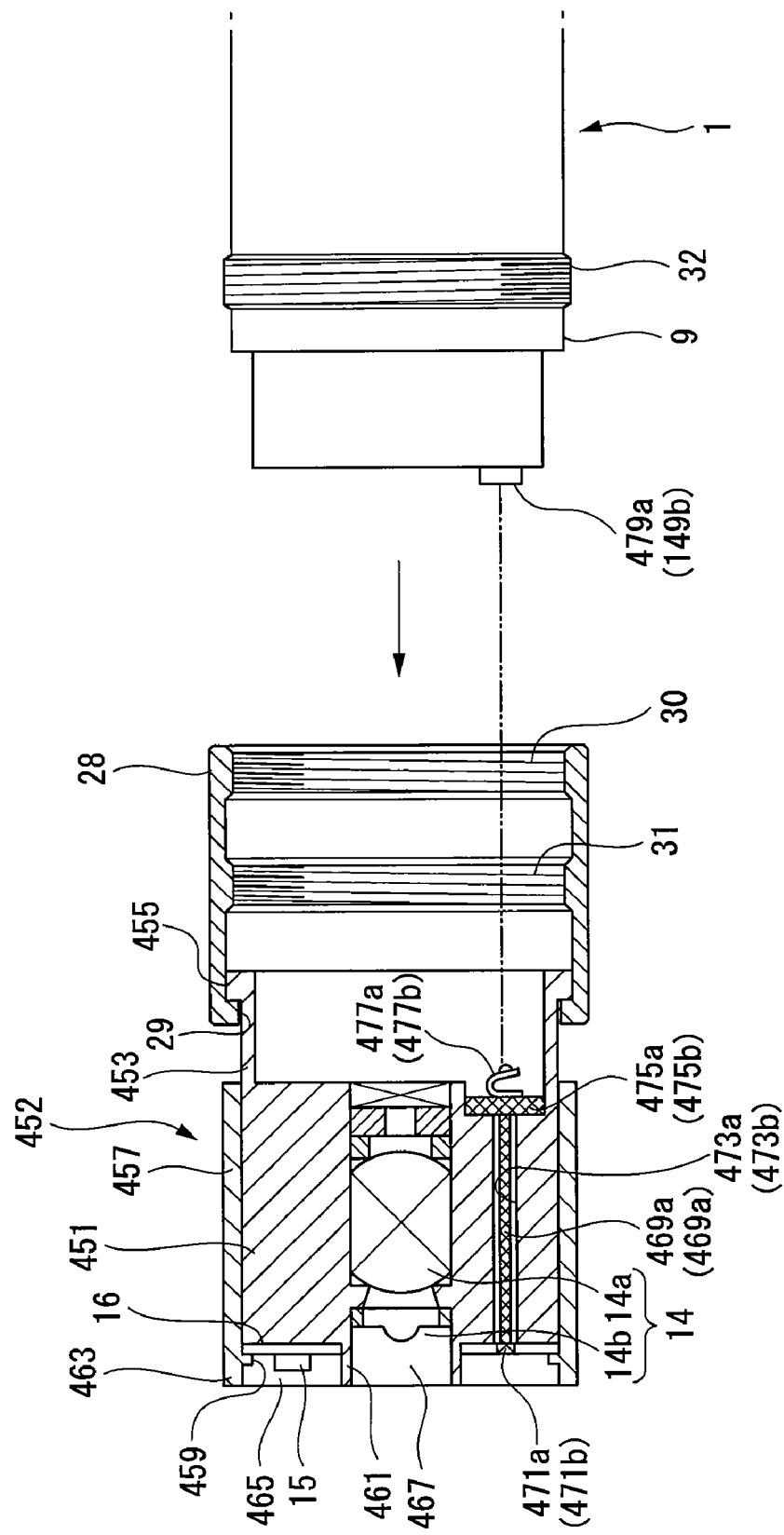
FIG. 10 is a longitudinal cross-sectional view of principal portions illustrating a sixth embodiment of the present invention.
Figure 11:
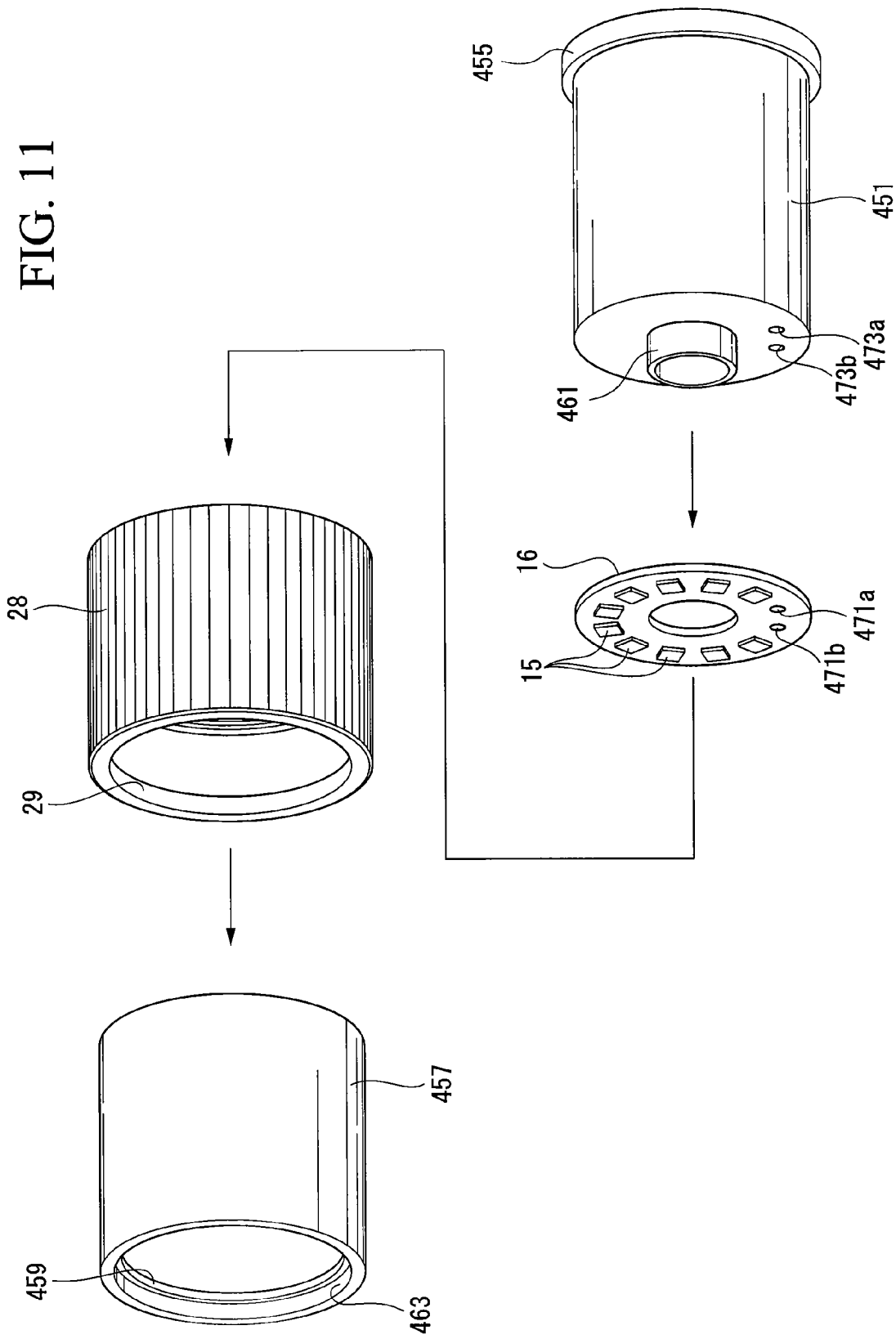
FIG. 11 is an exploded perspective view illustrating a sixth embodiment of the present invention.

Namely, as in the sixth embodiment shown in FIGS. 10 and 11, it is also possible for a substantially circular cylinder-shaped guide portion (i.e., connecting portion) 453 that has the same outer diameter as an LED supporting block 451 to be formed integrally with the LED supporting block 451 and protruding from a rear end portion thereof. A toroidal step portion 455 is formed on a rear end portion of the guide portion 453 so as to protrude outwards in a radial direction from an outer circumferential surface thereof and abut against the stopper flange 29 of the connecting ring 28.

In this structure, a stopper flange (i.e., abutting wall portion) 459 is formed extending inwards in a radial direction on an inner circumferential surface at a position slightly down from a front end portion of an adaptor housing (i.e., an outer cylindrical portion) 457. When the LED supporting block 451 is inserted from a rear end portion of the adaptor housing 457, this stopper flange 459 performs the function of abutting against a front end portion of the LED supporting block 451 that is positioned at the front in the insertion direction.

This structure will now be described in more detail. A placement surface of the LED chips 15 that have been placed at a front surface of the LED supporting block 451 abuts against the stopper flange 459 of the adaptor housing 457. Namely, of the non-conductive plate-shaped component 16 that is mounted on a front surface of the LED supporting block 451, the front surface thereof where the LED chips 15 are located abuts against the stopper flange 459.

As has been described above, by forming the guide portion 453 integrally with the LED supporting block 451, the number of constituent components of the lens adaptor 452 can be reduced, thereby allowing a reduction in the production costs of the lens adaptor 452 to be achieved and enabling the task of assembling the lens adaptor 452 to be performed easily. Moreover, because it is possible for heat generated from the LED chips 15 to be released to the flexible tube 1 via only two components, namely, the LED supporting block 451 and the connecting ring 28, heat discharge from the LED chips 15 can be performed efficiently.

When this type of structure is employed, because the LED chips 15 are placed further to the front of the adaptor housing 457 than the stopper flange 459 which protrudes inwards in a radial direction, it is possible to prevent any light from the LED chips 15 being blocked by the stopper flange 457. Accordingly, light can be irradiated over a wide angle by the LED chips 15.

In the structure of this sixth embodiment, a small-diameter cylindrical wall 461 is formed protruding from an inner circumferential edge of a front surface of the LED supporting block 451, and the non-conductive plate-shaped component 16 is placed on the front surface of the LED supporting block 451 with this cylindrical wall 461 in a state of being inserted in the hole in the non-conductive plate-shaped component 16. Furthermore, a large-diameter cylindrical wall 463 is formed on the adaptor housing 457 so as to protrude forward beyond the stopper flange 459. Accordingly, a substantially toroidal recessed portion 465 that is bounded by the pair of cylindrical walls 461 and 463 and by the non-conductive plate-shaped component 16, and a recessed portion 467 that is bounded by the cylindrical wall 461 of the LED supporting block 451 and the second lens group 14b may be filled with a transparent resin or a transparent cover glass may be placed thereon so that the second lens group 14b and the LED chips 15 can be protected by the resin or cover glass.

In the above described first through fifth embodiments, a pair of wires that supply current to the LED chips 15 are placed at point symmetrical positions on the outer circumferential surface of the LED supporting blocks (see FIGS. 1 and 3), however, as in the sixth embodiment shown in FIGS. 10 and 11, it is also possible for a pair of wires 469a and 469b to be positioned adjacent to each other.

Namely, a pair of electrodes 471a and 471b that are electrically connected to the plurality of LED chips 15 are embedded in the non-conductive plate-shaped component 16 so as to be adjacent to each other. Moreover, the wires 469a and 469b are connected respectively to the two electrodes 471a and 471b, and each of these wires 469a and 469b are inserted through a pair of through holes 473a and 473b that penetrate from a front end portion of the LED supporting block 451 to a rear end portion thereof. The respective wires 469a and 469b are connected respectively to electrode substrates 475a and 475b that are provided at a rear end portion of the through holes 473a and 473b, and adaptor electrodes 477a and 477b that are made from an elastically deformable metal are connected respectively to a rear portion of each of the electrode substrates 475a and 475b.

In this structure, in order to supply current to a plurality of LED chips 15, it is sufficient simply to press the respective adaptor electrodes 477a and 477b using a pair of electrodes that are provided adjacent to each other at a distal end portion of the connecting plug 9.

Figure 12:
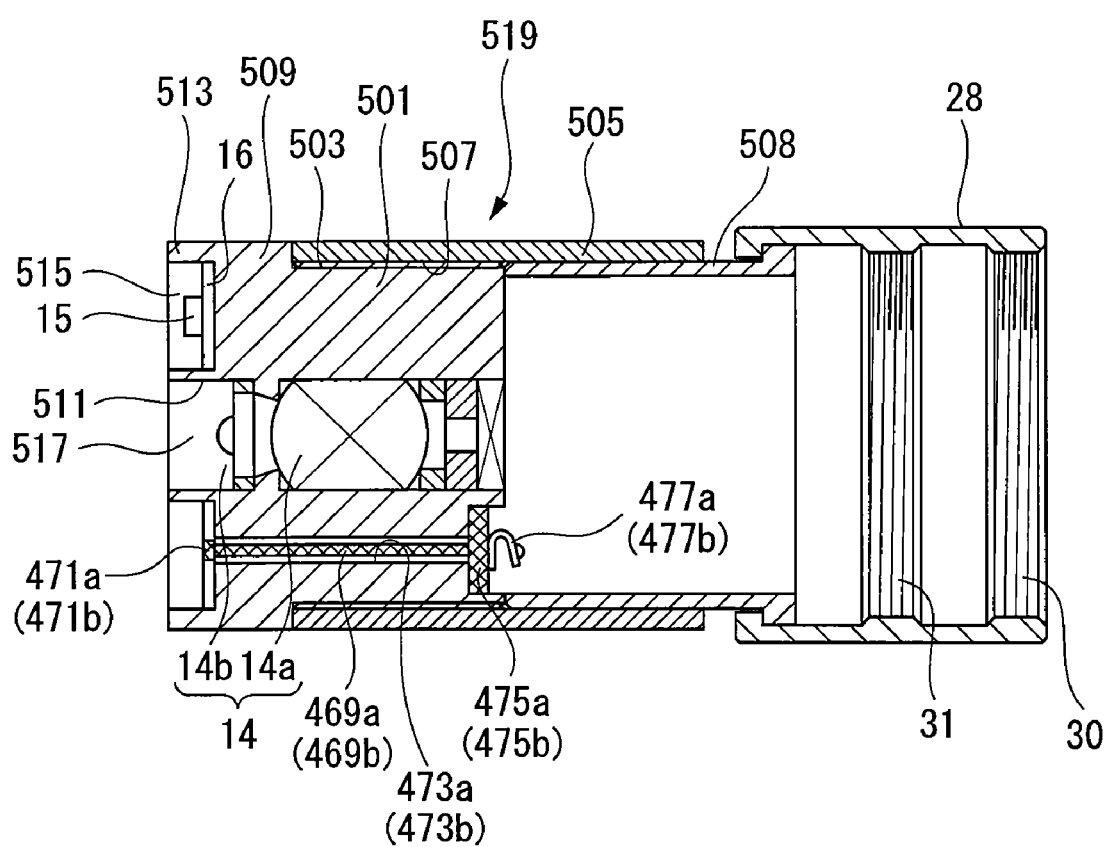
FIG. 12 is a longitudinal cross-sectional view of principal portions illustrating a seventh embodiment of the present invention.
Figure 13:
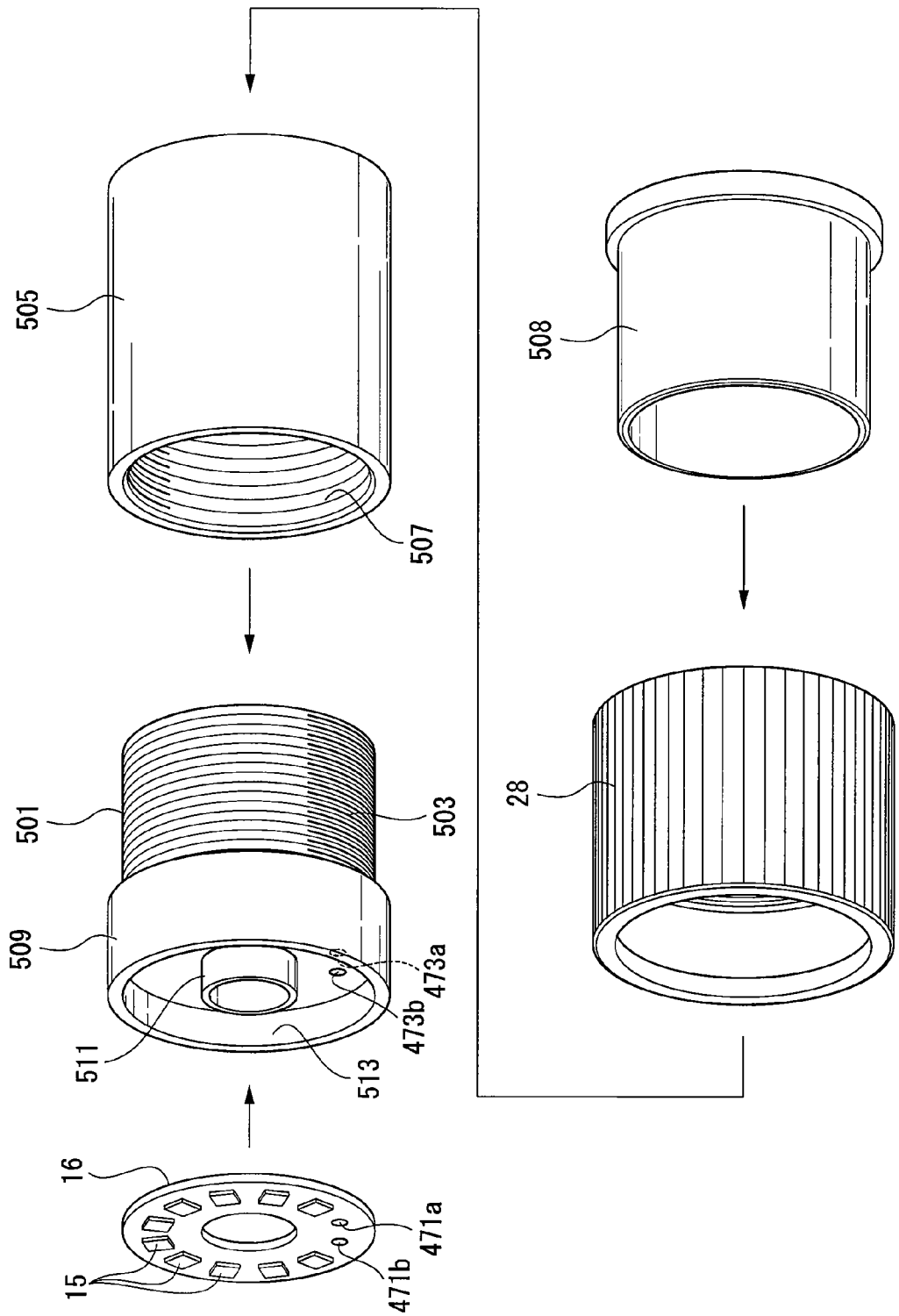
FIG. 13 is an exploded perspective view illustrating a seventh embodiment of the present invention.

In all of the above described embodiments the LED supporting block is inserted from the rear end portion of the adaptor housing, however, the present invention is not limited to this and it is also possible for the LED supporting block to be inserted from a front end portion of the adaptor housing. Namely, as in the seventh embodiment shown in FIGS. 12 and 13, it is possible to form a male thread 503 on an outer circumferential surface of an LED supporting block 501, and to form a female thread 507 on an inner circumferential surface located at a front end position of an adaptor housing (i.e., an outer cylindrical portion) 505. By then screwing the male thread 503 and the female thread 507 together, the LED supporting block 501 may be mounted on the adaptor housing 505. Note that, in this structure, a guide component 508 is inserted from a rear end portion of the adaptor housing 505.

A large-diameter step portion 509 that abuts against a front end surface of the adaptor housing 505 is formed on an outer circumferential surface of the LED supporting block 501. Accordingly, by screwing together the male thread 503 and the female thread 507, and also causing the step portion 509 to abut against the adaptor housing 505, relative positioning between the LED supporting block 501 and the adaptor housing 505 can be performed.

Moreover, this step portion 509 is located further to the rear in an axial direction than a placement surface of the LED supporting block 501 where the non-conductive plate-shaped component 16 is placed, namely, the placement surface of the LED supporting block 501 is located further to the front than the front end surface of the adaptor housing 505. Accordingly, the adaptor housing 505 that is located on the outer side in the radial direction of the LED supporting block 501 does not block the light from the LED chips 15, and it becomes possible to irradiate light from the LED chips 15 over a wide angle.

In the structure of the seventh embodiment, a small-diameter cylindrical wall 511 is formed protruding from an inner circumferential edge of a front surface of the LED supporting block 501, and a large-diameter cylindrical wall 513 is formed protruding from an outer circumferential edge of the same front surface. Accordingly, in the same way as in the case of the sixth embodiment, a substantially toroidal recessed portion 515 that is bounded by the pair of cylindrical walls 511 and 513 and by the non-conductive plate-shaped component 16, and a recessed portion 517 that is bounded by the small-diameter cylindrical wall 511 and the second lens group 14b may be filled with a transparent resin or a transparent cover glass may be placed thereon so that the second lens group 14b and the LED chips 15 can be protected by the resin or cover glass.

Note that, as in this seventh embodiment, when a structure is employed in which the LED supporting block 501 and the guide component 508 are inserted into the adaptor housing 505 from different directions, then the adaptor housing 505 may be formed integrally with the LED supporting block 501. In this case, it is possible to reduce the number of constituent components of the lens adaptor 519 so that a reduction in production costs of the lens adaptor 519 can be achieved and the task of assembling the lens adaptor 519 can be performed easily. Furthermore, in this case, because components on which the LED chips 15 are mounted, such as the non-conductive plate-shaped component 16 and the LED supporting block 501, are exposed to the outside, the effect is achieved that heat from the LED chips 15 can be efficiently discharged to the outside.

Figure 14:
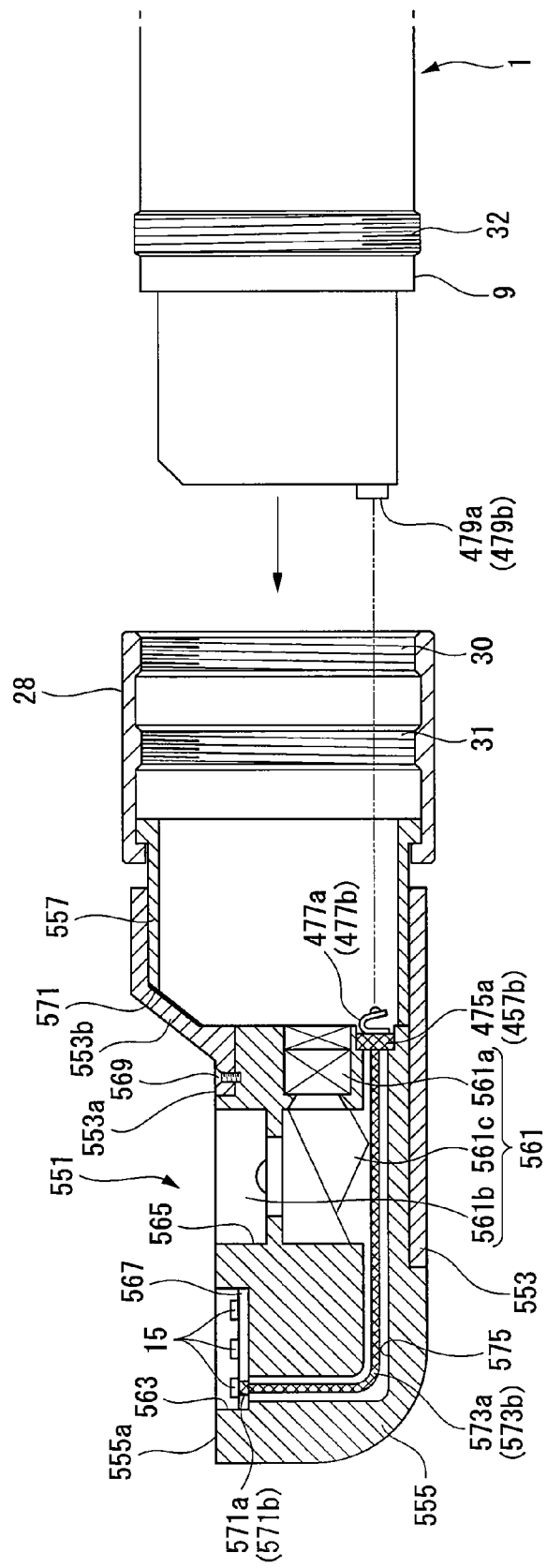
FIG. 14 is a longitudinal cross-sectional view of principal portions illustrating an eighth embodiment of the present invention.
Figure 15:
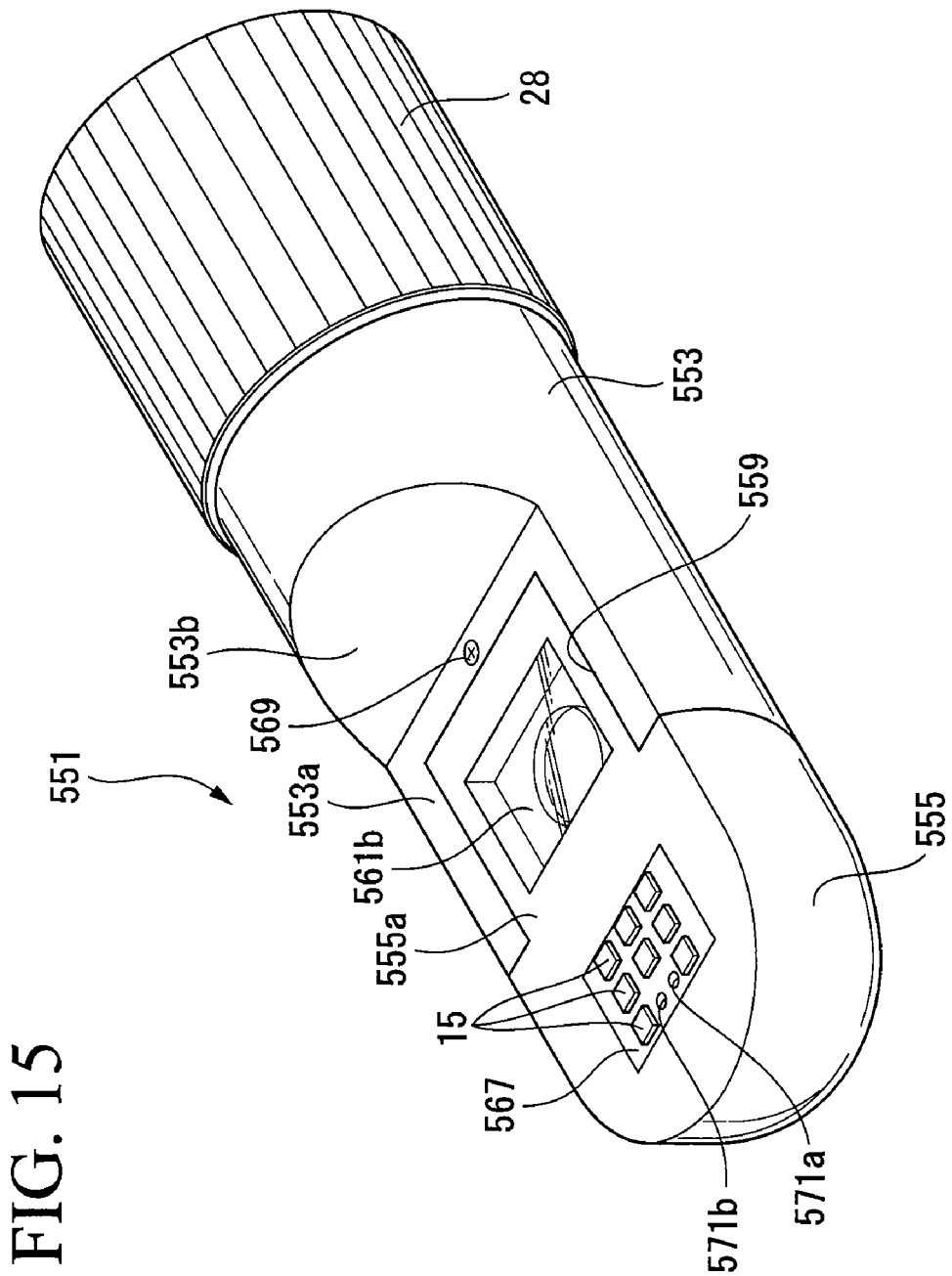
FIG. 15 is a perspective view illustrating an eighth embodiment of the present invention.
Figure 16:
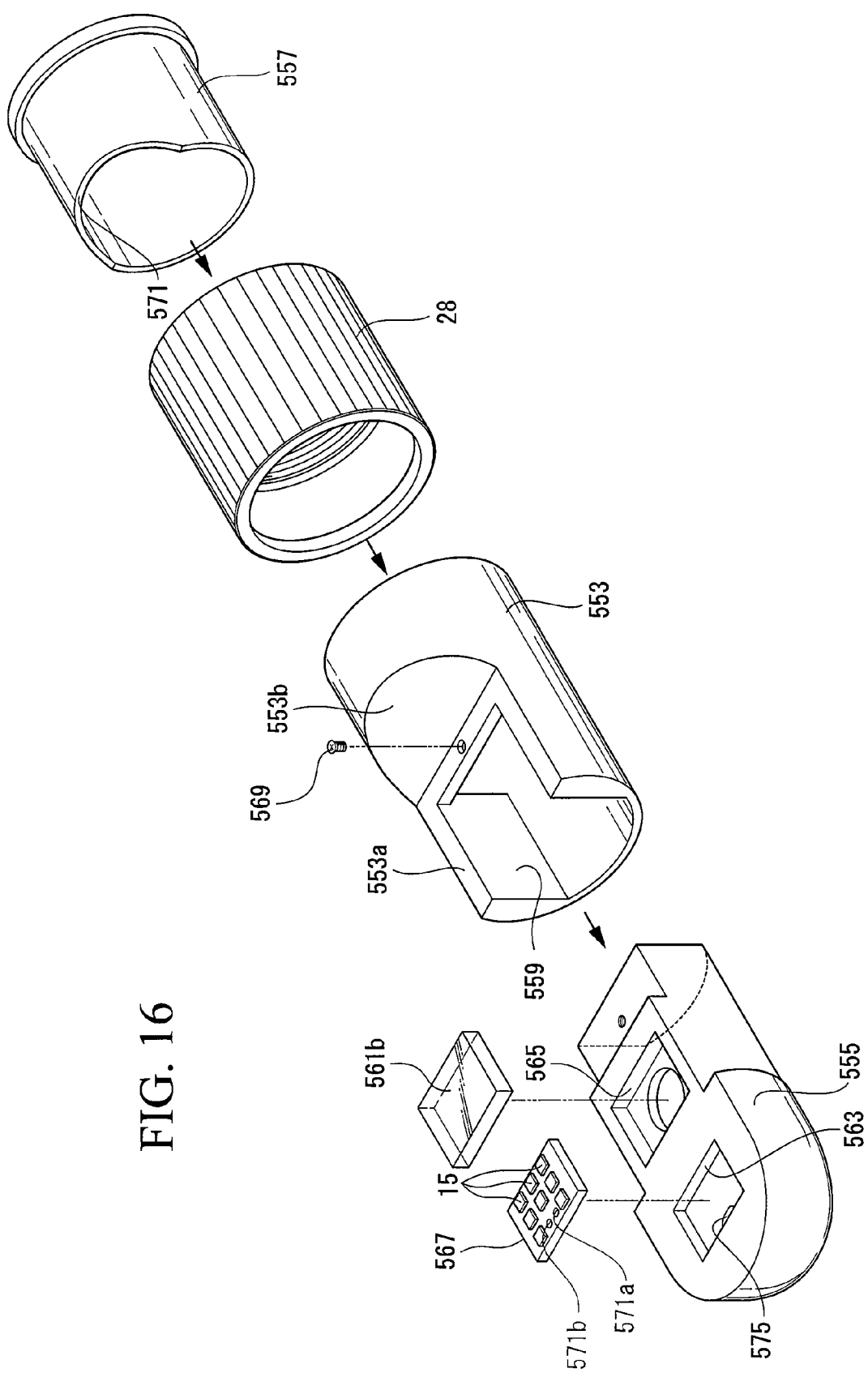
FIG. 16 is an exploded perspective view illustrating an eighth embodiment of the present invention.

FIGS. 14 to 16 show the eighth embodiment of the present invention. In the endoscope device of this embodiment, the basic structure of the present invention is applied to a side-view type of lens adaptor 551. In the lens adaptor 551 of this endoscope device, an LED supporting block 555 is inserted from a front end portion of a substantially cylindrical adaptor housing (i.e., an outer cylinder portion) 553, and a guide component 557 (i.e., a connecting component) 557 is inserted from a rear end portion of the adaptor housing 553.

A flat side surface 553a that extends in the longitudinal direction of the lens adaptor 553 is formed on a portion of an outer surface of the front end portion of the adaptor housing 553. A cut-out portion 559 that is cut out from the front end portion of the adaptor housing 553 is formed in the side surface 553a. The rear end portion of the adaptor housing 553 is formed in a substantially circular cylinder shape. Furthermore, a step portion 553b that connects together the front end portion side surface 553a and the rear end portion outer circumferential surface is formed at an intermediate portion of the adaptor housing 553.

An objective lens group 561 and a plurality of LED chips 15 are provided on the LED supporting block 555. The objective lens group 561 is formed by a first lens group 561a that is placed on the guide component 557 side, a second lens group 561b that is placed at a position where it is exposed to the outside through a side surface of the LED supporting block, and a prism 561c that is placed between the first lens group 561a and the second lens group 561b. The prism 561c alters an optical path of light irradiated from the outside into the second lens group 561b so that it is irradiated into the first lens group 561a.

The second lens group 561b and the plurality of LED chips 15 are arranged in line on a flat side surface 555a of the LED supporting block 555. Specifically, a non-conductive plate-shaped component 567 on which the plurality of LED chips 15 are mounted and the second lens group 561b are placed respectively within two recessed portions 563 and 565 that are cut out from the side surface 555a. The portion above the non-conductive plate-shaped component 567 may be filled with a transparent resin or a transparent cover glass may be placed thereon so that the non-conductive plate-shaped component 567 can be protected by the resin or cover glass.

The above described LED supporting block 555 is fixed by a screw 569 to an inner surface in the intermediate portion of the adaptor housing 553. In a state in which the LED supporting block is fixed to the adaptor housing 553, the side surface 555a of the LED supporting block 555 is exposed to the outside through the cut-out portion 559, and a single flat surface is formed by the side surface 555a of the LED supporting block 555 and the side surface 553a of the adaptor housing 553.

A cut-out portion 571 is formed in a front end portion of the guide component 557 that is assembled with the connecting ring 28. This cut-out portion 571 is formed such that the guide component 557 abuts against both the rear end portion of the LED supporting block 555 and the step portion 553b of the adaptor housing 553. When the guide component 557 is assembled in the connecting ring 28, it is fixed to an inner surface of a rear portion of the adaptor housing 553 by a screw (not shown).

Note that a pair of electrodes 571a and 571b that are electrically connected to the plurality of LED chips 15 is embedded in the non-conductive plate-shaped component 567 so as to be adjacent to each other. Moreover, wires 573a and 573b are connected respectively to the two electrodes 571a and 571b, and each of these wires 573a and 573b are inserted through a guide hole 575 that penetrates from a bottom surface of the recessed portion 563 where the non-conductive plate-shaped component 567 is placed to a rear end portion of the LED supporting block 555. The respective wires 573a and 573b are connected respectively to the pair of electrode substrates 475a and 475b that are provided at a rear end portion of the guide hole 575, and to the adaptor electrodes 477a and 477b.

Accordingly, current can be supplied to the plurality of LED chips 15 by joining the connecting ring 28 to the distal end portion of the connecting plug 9, and pressing in the respective adaptor electrodes 477a and 477b using the pair of electrodes 479a and 479b that are provided adjacent to each other at a distal end portion of the connecting plug.

In the endoscope device of this embodiment, in the same way as in the endoscope device of the fifth embodiment, because all of the lens elements of the objective lens group 561 are provided on the LED supporting block 555, it is possible to reduce the number of components due to it no longer being necessary to place a separate lens supporting block at a rear portion of the LED supporting block 555, and there is also an improvement in the workability of the assembly task.

Moreover, because it is no longer necessary to place a separate lens supporting block on the inner side of the LED supporting block 555, it is possible to reduce the size of the outer diameter of the LED supporting block 555 and achieve a reduction in the size of the lens adaptor 551 without reducing the outer diameter of the objective lens group 561 more than is necessary.

Figure 17:
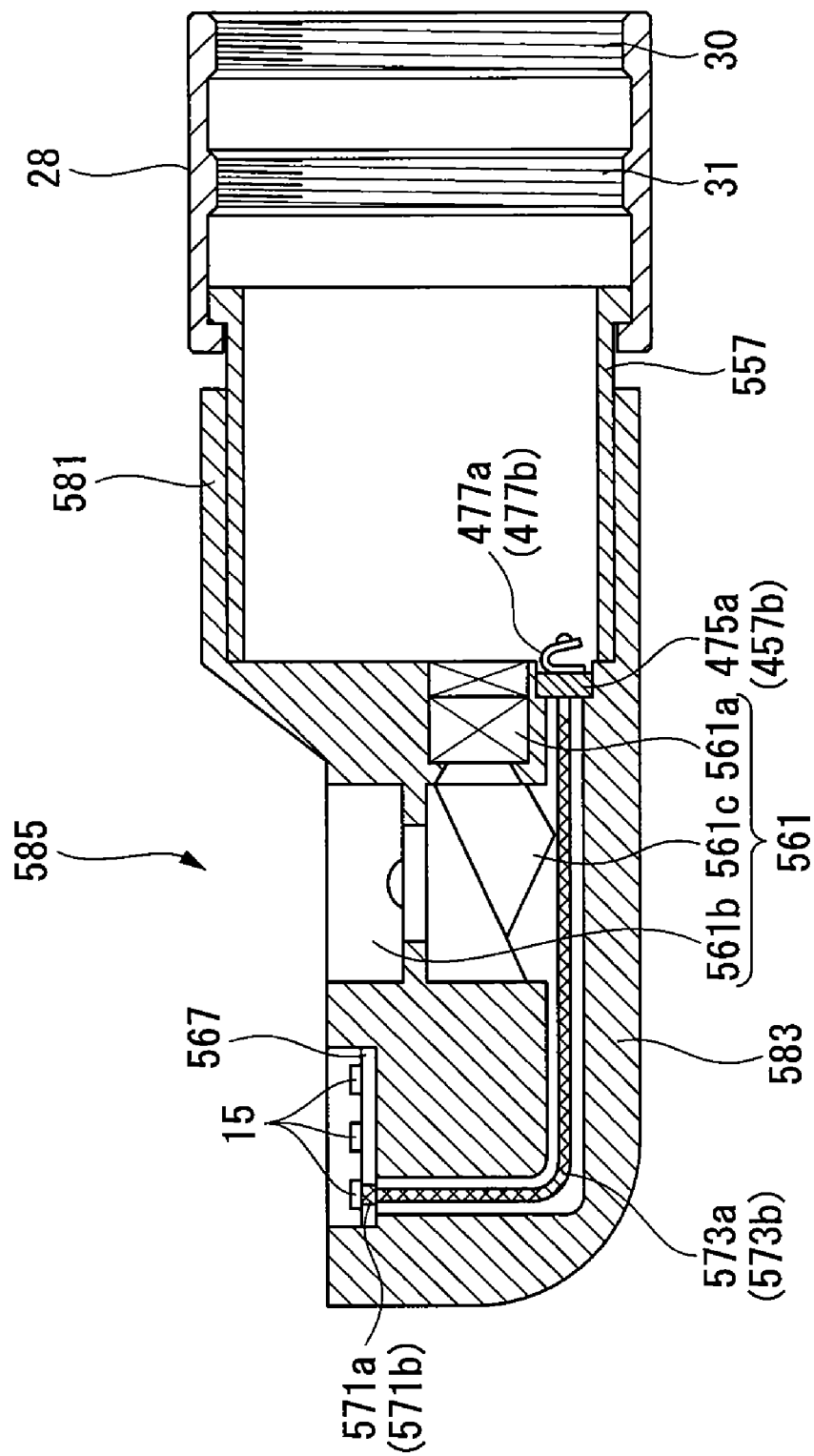
FIG. 17 is a longitudinal cross-sectional view of principal portions illustrating a ninth embodiment of the present invention.
Figure 18:
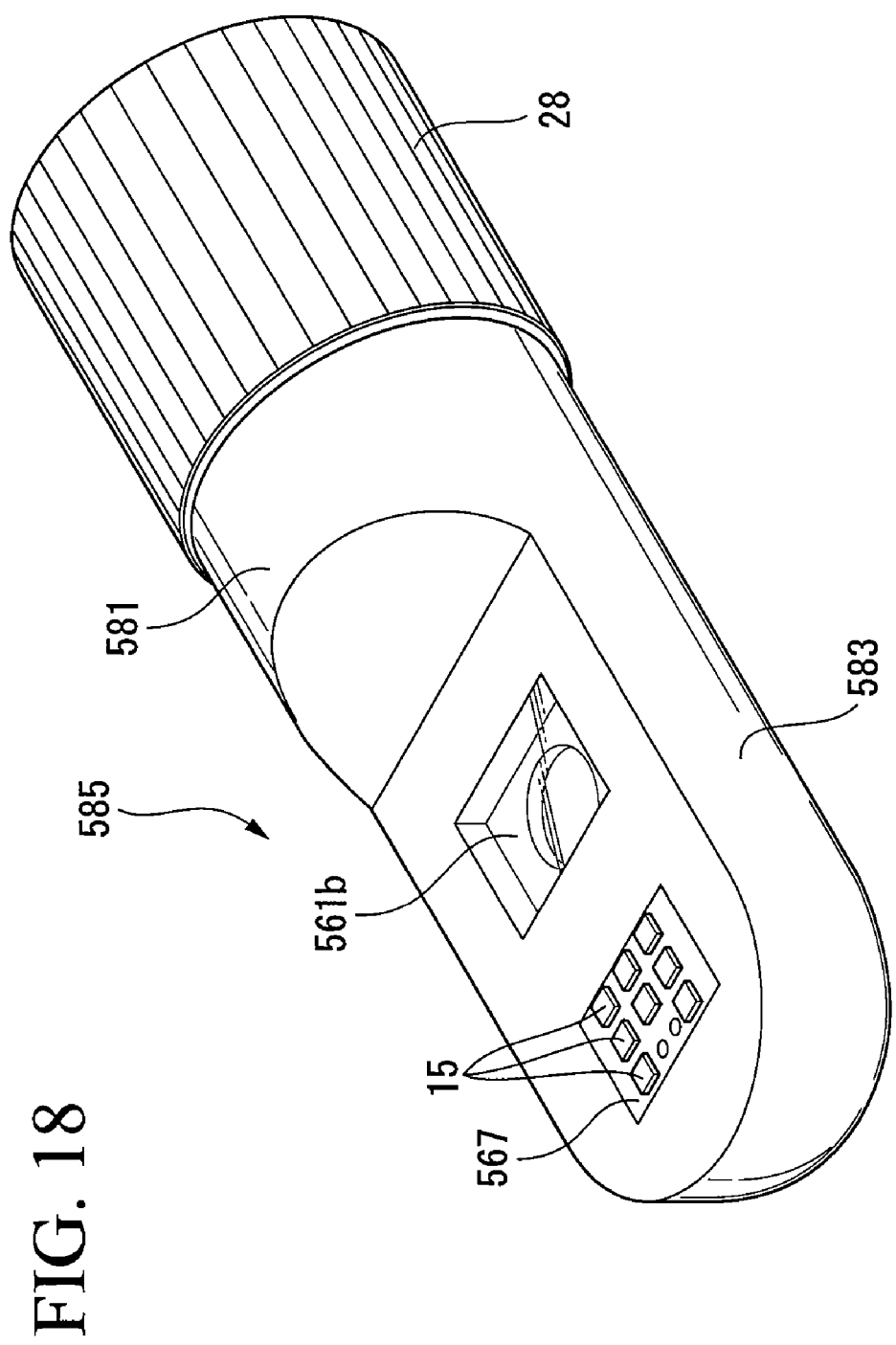
FIG. 18 is a perspective view illustrating a ninth embodiment of the present invention.

As in this eighth embodiment, when a structure is employed in which the LED supporting block 555 and the guide component 557 are inserted into the adaptor housing 553 from different directions, then, as in the ninth embodiment shown in FIGS. 17 and 18, a substantially circular cylinder-shaped adaptor housing (i.e., an outer cylinder portion) 581 may be formed integrally with a rear end portion of an LED supporting block 583. In this case, it is possible to reduce the number of constituent components of the lens adaptor 585. Accordingly, a reduction in production costs of the lens adaptor 585 can be achieved and the task of assembling the lens adaptor 585 can be performed easily.

Figure 19:
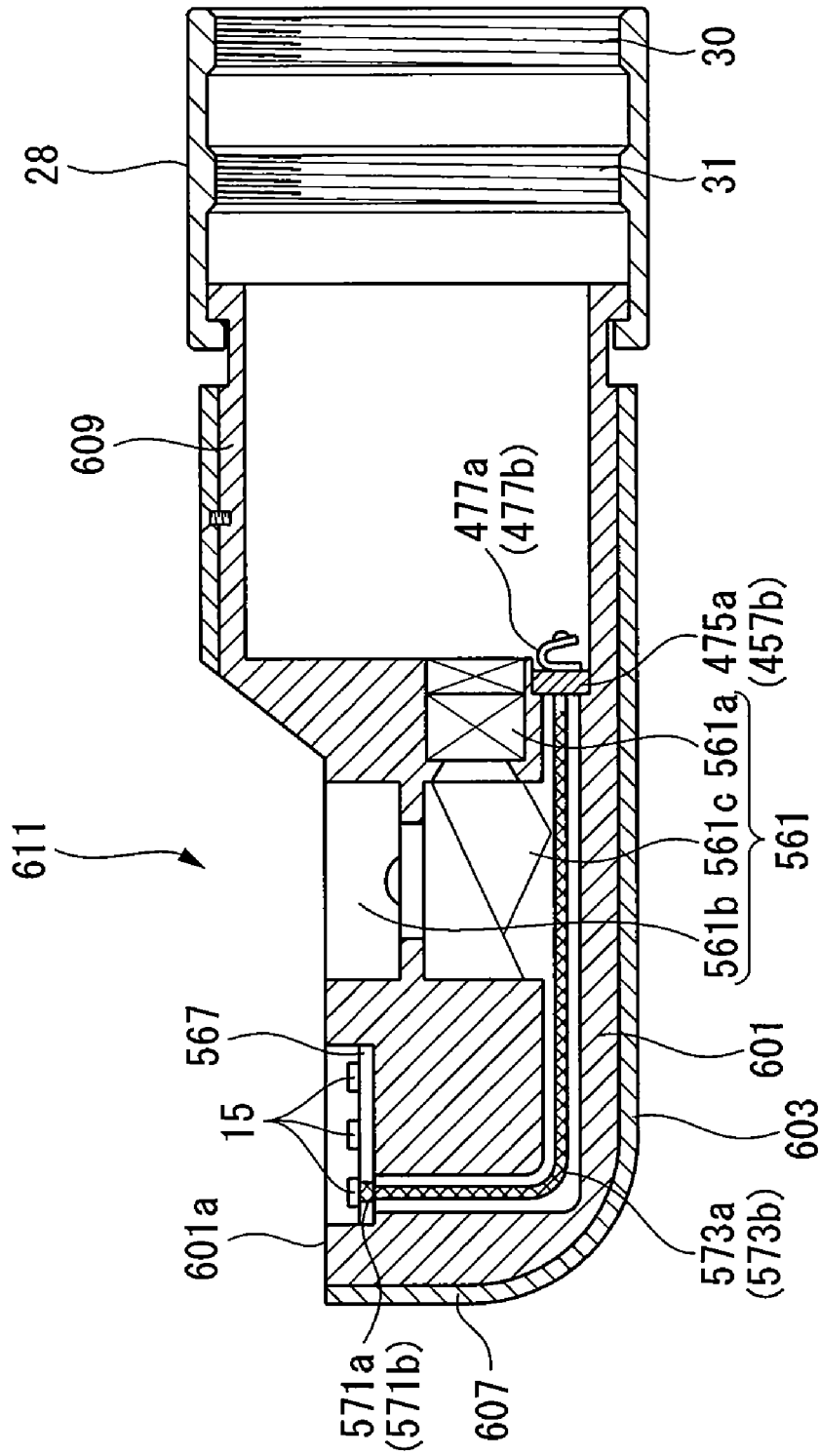
FIG. 19 is a longitudinal cross-sectional view of principal portions illustrating a tenth embodiment of the present invention.
Figure 20:
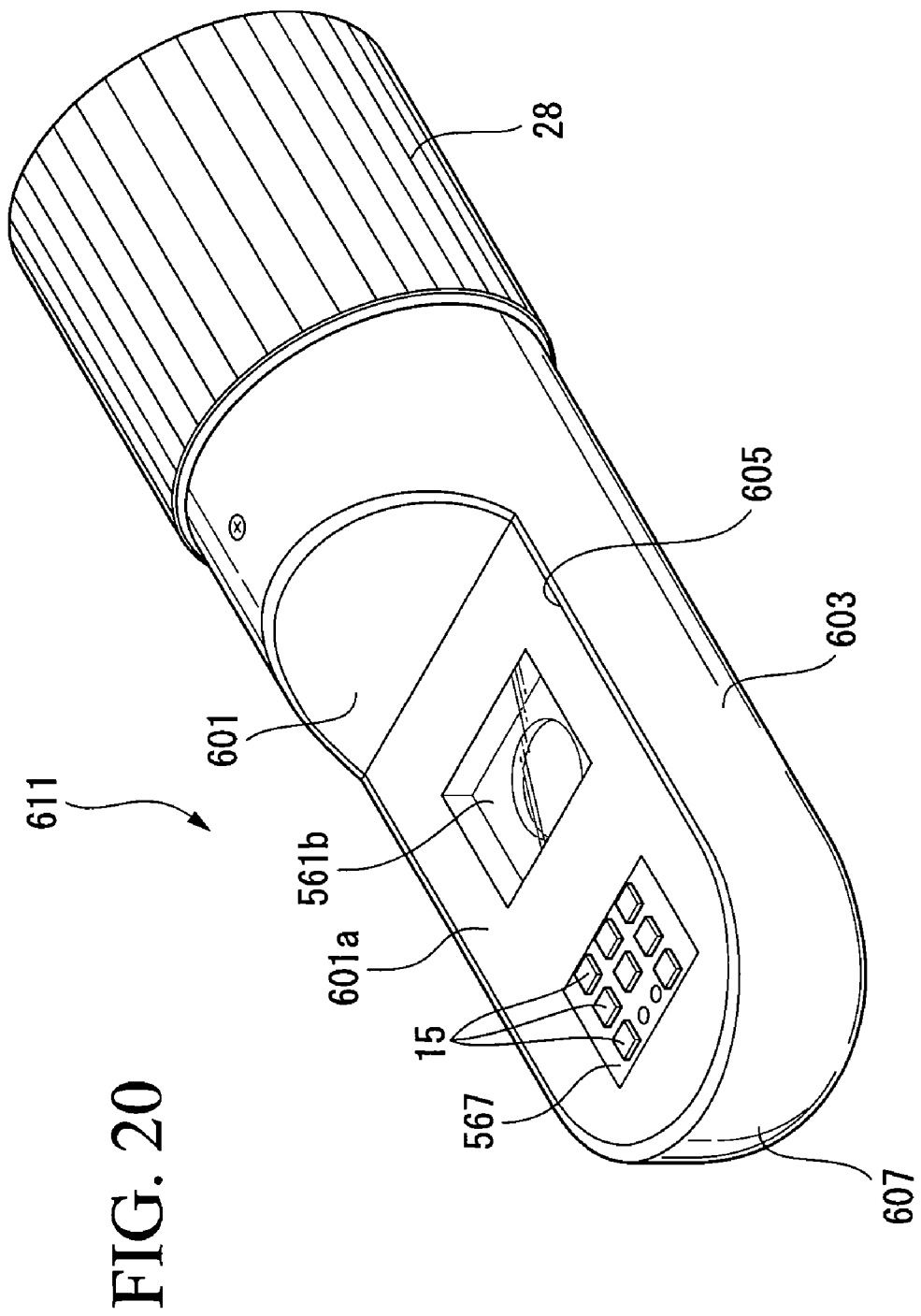
FIG. 20 is a perspective view illustrating a tenth embodiment of the present invention.
Figure 21:
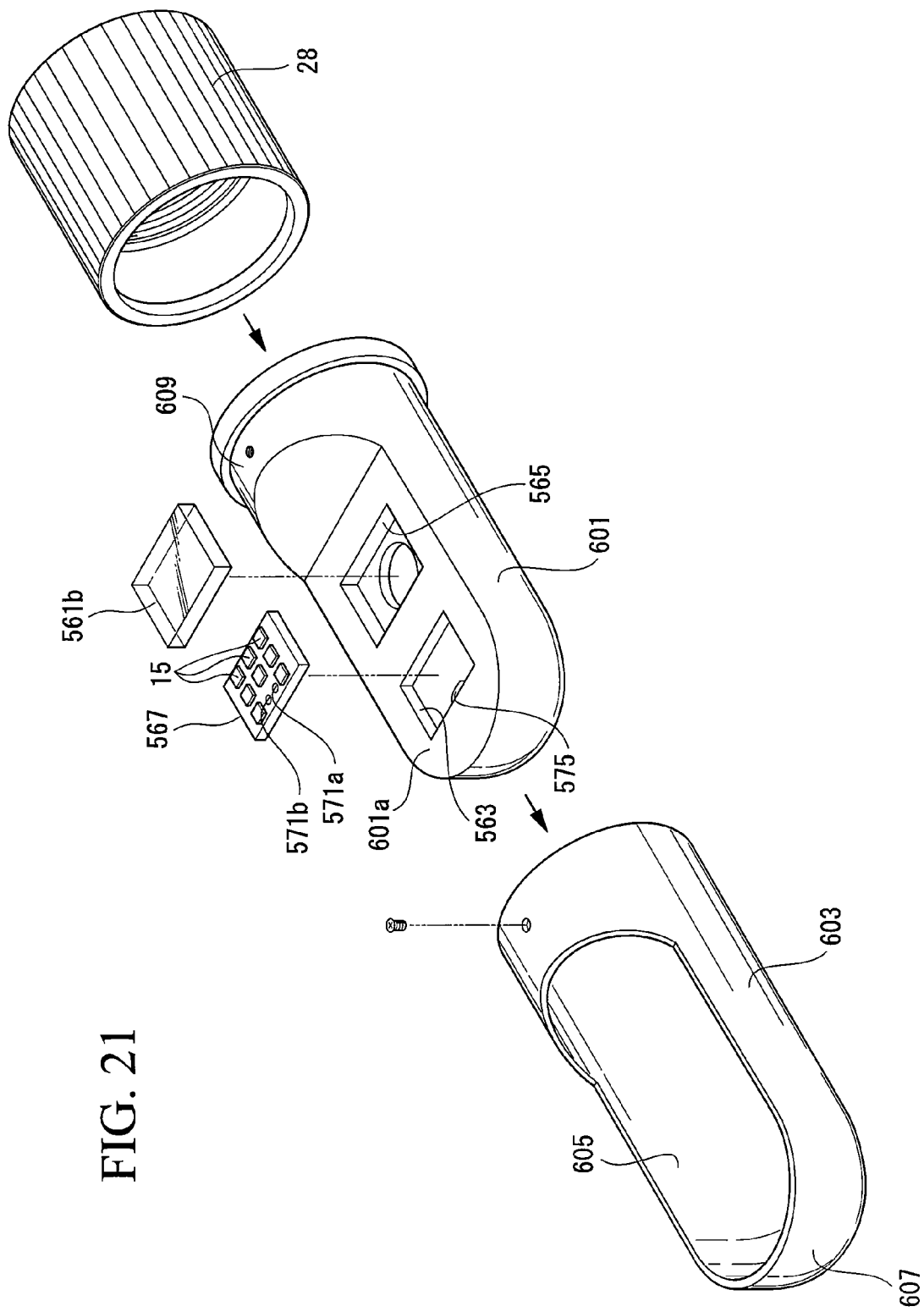
FIG. 21 is an exploded perspective view illustrating a tenth embodiment of the present invention.

Moreover, in the eighth embodiment, the LED supporting block 555 is inserted from the front end portion of the adaptor housing 553 (see FIGS. 14 to 16), however, the present invention is not limited to this and, as in the tenth embodiment shown in FIGS. 19 to 21, it is also possible for an LED supporting block 601 to be inserted from a rear end portion of an adaptor housing (i.e., an outer cylinder portion) 603 that is formed in a substantially circular cylinder shape.

An aperture portion 605 that exposes the plurality of LED chips 15 that are located on a side surface 601a of the LED supporting block 601 and a second lens group 561b to the outside, and also an end surface wall portion (i.e., an abutting wall portion) 607 that protrudes inwards from an outer surface of the adaptor housing 603 are formed at a front end portion of the adaptor housing 603. When the LED supporting block 601 is inserted from a rear end portion of the adaptor housing 603, the end surface wall portion 607 performs the function of abutting against a front end portion of the LED supporting block 601 that is positioned at the front in the insertion direction.

In the case of this structure, because it is possible to assemble a lens adaptor 611 by inserting the LED supporting block 601 together with a guide portion (i.e., connecting portion) 609 from the rear end portion of the adaptor housing 603, as is shown in the drawings, it is possible to form the guide portion 609, which is assembled with the connecting ring 28, integrally with the rear end portion of the LED supporting block 601.

Accordingly, the number of constituent components of the lens adaptor 611 can be reduced, thereby allowing a reduction in the production costs of the lens adaptor 611 to be achieved and enabling the task of assembling the lens adaptor 611 to be performed easily. Moreover, because it is possible for heat generated from the LED chips 15 to be released to the flexible tube 1 via only two components, namely, the LED supporting block 601 and the connecting ring 28, heat discharge from the LED chips 15 can be performed efficiently. Furthermore, because the components on which the LED chips 15 are mounted, such as the non-conductive plate-shaped component 16 and the LED supporting block 501, are exposed to the outside, the effect is achieved that heat from the LED chips 15 can be efficiently discharged to the outside.

Note that, if the efficiency of the heat discharge from the LED chips 15 is not a consideration, then it is also possible, for example, to disconnect the guide component 609 from the LED supporting block 601 and form it using a different component.

Figure 22:
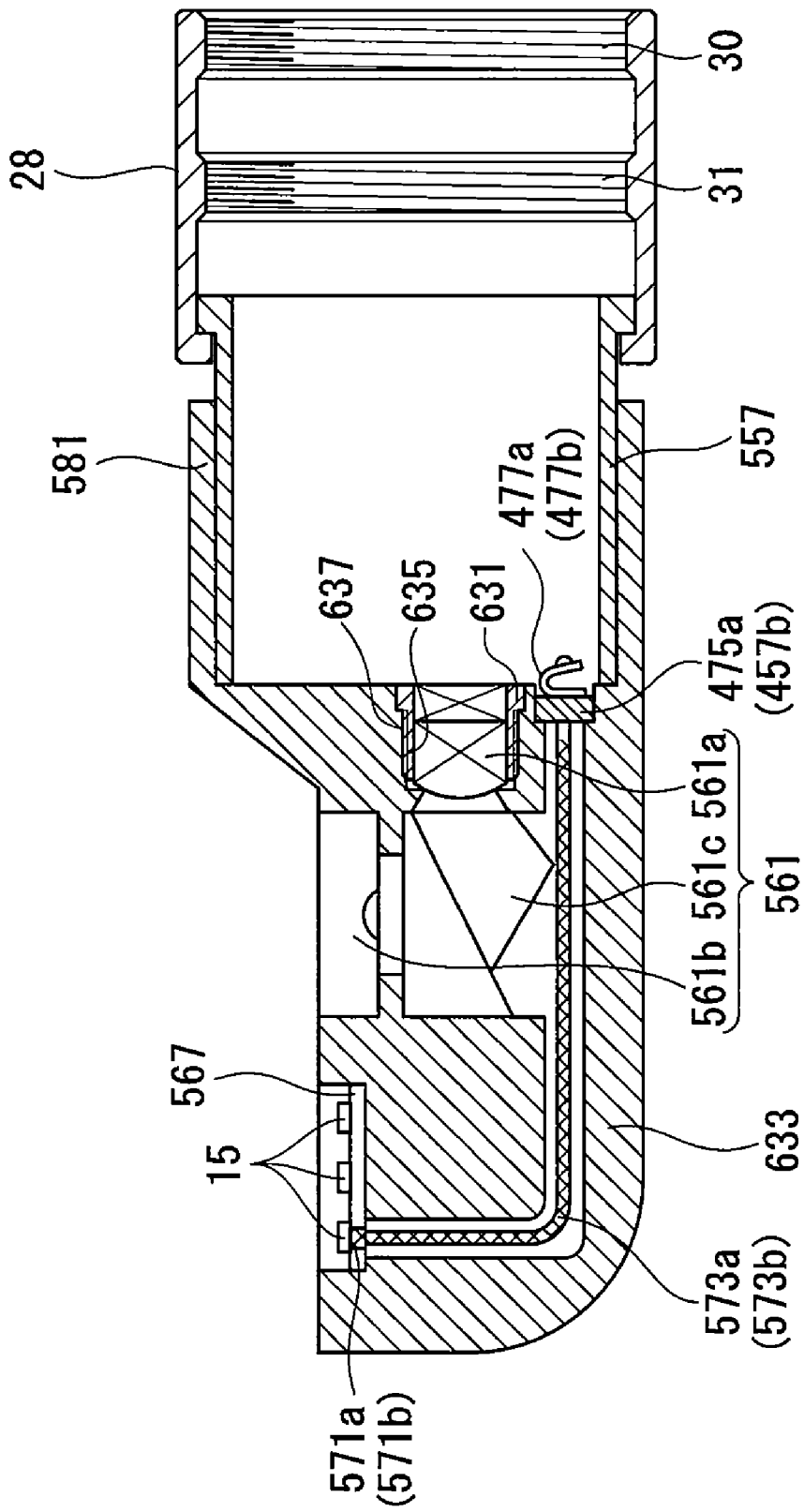
FIG. 22 is a longitudinal cross-sectional view of principal portions illustrating an eleventh embodiment of the present invention.

Moreover, in the eighth and ninth embodiments, all of the lens elements of the objective lens group 561 are mounted on the LED supporting block (see FIGS. 14 to 16), however, the present invention is not limited to this and, as in the eleventh embodiment shown in FIG. 22, it is also possible to mount a portion of the objective lens group 561 (i.e., the first lens group 561a that is located on the guide component 557 side) on a separate lens supporting block 631, and to mount the remainder of the constituent lenses (i.e., the second lens group 561b and the prism 561c) making up the objective lens group 561 on a lens supporting block 633.

An insertion hole that is cut out from a rear surface of the LED supporting block 633 and through which is inserted the lens supporting block 631 is formed in the lens supporting block 633, and a female thread 635 is formed on an inner circumferential surface of this insertion hole. The lens supporting block 631 is formed in a substantially circular cylinder shape, and a male thread 637 that screws into the female thread 635 of the LED supporting block 633 is formed on an outer circumferential surface of the lens supporting block 631. Namely, the LED supporting block 633 is able to be fitted onto and removed from the front surface of the lens supporting block 631 via the female screw 635 and the male screw 637.

In the case of this structure, by rotating the lens supporting block 631 relative to the LED supporting block 633 and also moving the position thereof forwards or backwards, it is possible to adjust the focus of the objective lens group 561.

It is also possible to remove the LED supporting block 633 from the front surface of the lens supporting block 631 and replace it, if necessary, with a an LED supporting block that is suitable for another application. At this time, the second lens group 561b of the lens supporting block 631 can be shared.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as limited by the foregoing description and is only limited by the scope of the appended claims.

The endoscope device of the present invention can be favorably used for industrial and medical applications.

What is claimed is:

1. An endoscope device comprising an insertion portion configured to be inserted into a lumen of a subject, the endoscope device comprising:
    an objective lens group positioned at a distal end of the insertion portion and used to observe or to photograph the subject; and
    an illumination device positioned at the distal end of the insertion portion and configured to illuminate the subject and including a LED including LED chips and an LED chip supporting block that supports the LED chips, and at least a portion of the objective lens group is mounted on the LED supporting block,
    wherein a lens adapter is provided with the LED chips and the LED supporting block and is positioned at a distal end of an insertion portion main body of the insertion portion, the lens adapter comprising:
    a substantially cylindrical outer cylinder portion positioned at a front end portion and through which is inserted the LED supporting block;
    a substantially cylindrical connecting portion inserted through the outer cylinder portion and fixed to a rear end portion of the outer cylinder portion; and a substantially cylindrical connecting ring mounted on the connecting portion so as to be freely rotatable, and configured to connect the LED supporting block to a distal end of the insertion portion main body so as to be freely attached thereto and to be removed therefrom, and a threaded portion screwed into a distal end of the insertion portion main body is formed on the connecting ring, wherein an abutting wall portion that protrudes inwards is provided at a front end portion of the outer cylindrical portion, and when the LED supporting block is inserted from a rear end portion of the outer cylindrical portion, a front end portion of the LED supporting block that is positioned at the front in the insertion direction of the LED supporting block abuts against the abutting wall portion.

2. The endoscope device according to claim 1, wherein the entire objective lens group is mounted on the LED supporting block.

3. An endoscope device comprising an insertion portion configured to be inserted into a lumen of a subject, the endoscope device comprising:

an objective lens group positioned at a distal end of the insertion portion and used to observe or to photograph the subject; and an illumination device positioned at the distal end of the insertion portion and configured to illuminate the subject and including a LED including LED chips and an LED chip supporting block that supports the LED chips, and at least a portion of the objective lens group is mounted on the LED supporting block, wherein a lens adapter is provided with the LED chips and the LED supporting block and is positioned at a distal end of an insertion portion main body of the insertion portion, the lens adapter comprising:

a substantially cylindrical connecting portion inserted through the outer cylinder portion and fixed to a rear end portion of the outer cylinder portion; and a substantially cylindrical connecting ring mounted on the connecting portion so as to be freely rotatable, and configured to connect the LED supporting block to a distal end of the insertion portion main body so as to be freely attached thereto and to be removed therefrom, and a threaded portion screwed into a distal end of the insertion portion main body is formed on the connecting ring, wherein a stopper flange that protrudes inwards in a radial direction is formed at a front end portion of the outer cylinder portion, and the stopper flange abuts against a placement surface for the LED chips located on a front surface of the LED supporting block.

4. The endoscope device according to claim 3, wherein the entire objective lens group is mounted on the LED supporting block.

5. An endoscope device comprising an insertion portion configured to be inserted into a lumen of a subject, the endoscope device comprising:

an objective lens group positioned at a distal end of the insertion portion and used to observe or to photograph the subject; and an illumination device positioned at the distal end of the insertion portion and configured to illuminate the subject and including a LED including LED chips and an LED chip supporting block that supports the LED chips, and at least a portion of the objective lens group is mounted on the LED supporting block, wherein a lens adapter is provided with the LED chips and the LED supporting block and is positioned at a distal end of an insertion portion main body of the insertion portion, the lens adapter comprising:

a substantially cylindrical outer cylinder portion positioned at a front end portion and through which is inserted the LED supporting block;

a substantially cylindrical connecting portion inserted through the outer cylinder portion and fixed to a rear end portion of the outer cylinder portion; and a substantially cylindrical connecting ring mounted on the connecting portion so as to be freely rotatable, and configured to connect the LED supporting block to a distal end of the insertion portion main body so as to be freely attached thereto and to be removed therefrom, and a threaded portion screwed into a distal end of the insertion portion main body is formed on the connecting ring, wherein the placement surface for the LED chips located on the front surface of the LED supporting block is positioned so as to protrude from a front end portion of the outer cylinder portion.

6. The endoscope device according to claim 5, wherein the entire objective lens is mounted on the LED supporting block.

* * * * *

UNITED STATES PATENT AND TRADEMARK OFFICE
CERTIFICATE OF CORRECTION

PATENT NO.         : 7,749,160 B2                                                              Page 1 of 1
APPLICATION NO.    : 11/616221
DATED              : July 6, 2010
INVENTOR(S)        : Yasuo Hirata It is certified that error appears in the above-identified patent and that said Letters Patent is hereby corrected as shown below:

Title Page, Item (63) should read:

(63)   Continuation of application No. PCT/JP2005/011634,
       Filed on Jun. 24, 2005

Signed and Sealed this
Twenty-third Day of August, 2011

David J. Kappos
*Director of the United States Patent and Trademark Office*